US012163918B1

(12) United States Patent
McElroy et al.

(10) Patent No.: US 12,163,918 B1
(45) Date of Patent: Dec. 10, 2024

(54) COMPOSITIONS AND METHODS FOR PROTEIN ELECTROPHORESIS

(71) Applicant: ProteinSimple, San Jose, CA (US)

(72) Inventors: James McElroy, San Jose, CA (US); Christopher Heger, Campbell, CA (US); Annegret Boge, Menlo Park, CA (US); Irina Georgievna Kazakova, San Jose, CA (US)

(73) Assignee: ProteinSimple, San Jose, CA (US)

( * ) Notice: Subject to any disclaimer, the term of this patent is extended or adjusted under 35 U.S.C. 154(b) by 0 days.

(21) Appl. No.: 18/311,005

(22) Filed: May 2, 2023

Related U.S. Application Data

(63) Continuation of application No. 16/549,946, filed on Aug. 23, 2019, now abandoned.

(60) Provisional application No. 62/797,127, filed on Jan. 25, 2019, provisional application No. 62/722,017, filed on Aug. 23, 2018.

(51) Int. Cl.
| | | |
|---|---|---|
| *G01N 27/447* | (2006.01) | |
| *C07C 9/08* | (2006.01) | |
| *C07D 265/28* | (2006.01) | |
| *C07K 16/24* | (2006.01) | |
| *C07K 16/28* | (2006.01) | |

(52) U.S. Cl.
CPC ......... *G01N 27/44747* (2013.01); *C07C 9/08* (2013.01); *C07D 265/28* (2013.01); *C07K 16/241* (2013.01); *C07K 16/2887* (2013.01)

(58) Field of Classification Search
None
See application file for complete search history.

(56) References Cited

U.S. PATENT DOCUMENTS

| | | |
|---|---|---|
| 5,045,172 A | 9/1991 | Guzman |
| 5,180,475 A | 1/1993 | Young et al. |
| 5,274,240 A | 12/1993 | Mathies et al. |
| 5,338,427 A | 8/1994 | Shartle et al. |
| 5,384,024 A | 1/1995 | Moring et al. |
| 5,395,502 A | 3/1995 | Pawliszyn |
| 6,083,372 A | 7/2000 | Grover et al. |
| 6,087,188 A | 7/2000 | Johansen et al. |
| 6,093,300 A | 7/2000 | Hayashizaki et al. |
| 6,126,870 A | 10/2000 | Akhavan-Tafti |
| 6,165,800 A | 12/2000 | Jiang et al. |
| 6,287,767 B1 | 9/2001 | Bronstein et al. |
| 6,395,503 B1 | 5/2002 | Suzuki et al. |
| 6,689,576 B2 | 2/2004 | Matsuno et al. |
| 7,336,355 B2 | 2/2008 | Ishibashi et al. |
| 7,935,308 B2 | 5/2011 | O'Neill et al. |
| 8,778,155 B2 | 7/2014 | Tsai et al. |
| 10,794,860 B2 | 10/2020 | Roach et al. |
| 11,726,058 B2 | 8/2023 | Roach et al. |
| 2002/0123073 A1 | 9/2002 | Amirkhanian et al. |
| 2002/0162744 A1* | 11/2002 | Nouadje .......... G01N 27/44747 204/451 |
| 2003/0116436 A1 | 6/2003 | Amirkhanian et al. |
| 2003/0132113 A1 | 7/2003 | Sarme et al. |
| 2006/0127275 A1 | 6/2006 | Holl et al. |
| 2007/0131870 A1 | 6/2007 | Pang et al. |
| 2010/0140505 A1 | 6/2010 | Pang et al. |
| 2011/0011740 A1 | 1/2011 | Roach et al. |
| 2012/0274760 A1 | 11/2012 | King et al. |
| 2013/0001084 A1 | 1/2013 | Dolnik |
| 2015/0090591 A1 | 4/2015 | Yang et al. |
| 2015/0093304 A1 | 4/2015 | Guzman |
| 2015/0258548 A1 | 9/2015 | Bird et al. |
| 2015/0346151 A1 | 12/2015 | Boeke et al. |
| 2016/0077053 A1 | 3/2016 | Onuma |
| 2017/0174721 A1* | 6/2017 | Goklen .............. B01D 15/1871 |
| 2018/0202968 A1 | 7/2018 | Singer et al. |
| 2018/0282782 A1* | 10/2018 | Clark ................. G01N 33/6803 |
| 2018/0321189 A1 | 11/2018 | Roach et al. |
| 2021/0231607 A1 | 7/2021 | Roach et al. |
| 2024/0183820 A1 | 6/2024 | Roach et al. |

FOREIGN PATENT DOCUMENTS

| | | |
|---|---|---|
| CN | 1806169 A | 7/2006 |
| CN | 101115985 A | 1/2008 |
| CN | 103328963 A | 9/2013 |
| CN | 104902817 A | 9/2015 |
| EP | 0329779 A1 | 8/1989 |
| EP | 0339779 A2 | 11/1989 |
| JP | H10197480 A | 7/1998 |
| JP | 2000065796 A | 3/2000 |
| JP | 2001289820 A | 10/2001 |
| JP | 2004532384 A | 10/2004 |
| JP | 2008506970 A | 3/2008 |
| JP | 2010243498 A | 10/2010 |
| JP | 2012118046 A | 6/2012 |
| JP | 2013536439 A | 9/2013 |
| WO | WO-9917111 A1 | 4/1999 |
| WO | WO-02059589 A2 | 8/2002 |
| WO | WO-2004061418 A2 | 7/2004 |
| WO | WO-2012027175 A2 | 3/2012 |
| WO | WO-2013181352 A1 | 12/2013 |
| WO | WO-2015048458 A2 | 4/2015 |
| WO | WO-2015134945 A1 | 9/2015 |

OTHER PUBLICATIONS

Extended European Search Report for European Application No. 17739061.4, mailed Jul. 31, 2019, 8 pages.

(Continued)

*Primary Examiner* — J. Christopher Ball

(74) *Attorney, Agent, or Firm* — COOLEY LLP

(57) ABSTRACT

Compositions and methods for protein electrophoresis are described herein. In various embodiments, the compositions and methods of the disclosure provide for reduced protein fragmentation relative to the protein fragmentation caused by alternative compositions and methods.

22 Claims, 25 Drawing Sheets

(56) References Cited

OTHER PUBLICATIONS

First Office Action for Chinese Application No. 201780015587.5, mailed May 22, 2020, 19 pages.
International Search Report and Written Opinion for International Application No. PCT/US2017/013470, mailed Jun. 9, 2017, 14 pages.
Notice of Reasons for Rejection for Japanese Application No. 2018-536474, mailed Aug. 25, 2021, 7 pages.
Notice of Reasons for Rejection for Japanese Application No. 2018-536474, mailed Nov. 30, 2020, 11 pages.
Office Action for U.S. Appl. No. 16/033,808, mailed Feb. 14, 2020, 38 pages.
Second Office Action for Chinese Application No. 201780015587.5, mailed Feb. 4, 2021, 7 pages.
Takara, "EDTA Buffer Powder," product description, 2021, 1 page, accessed online at https://www.takarabio.com/products/protein-research/sds-page-and-western-blotting/buffers-and-powders/edta-powder.
Zhang, J. et al., "Method development and validation of capillary sodium dodecyl sulfate gel electrophoresis for the characterization of a monoclonal antibody," J. Pharm Biomed Anal. Dec. 15, 2010;53(5):1236-1243.
Office Action and Search report for Chinese Patent Application No. CN202110833777.6, dated Jan. 17, 2024, 20 pages.
Office Action for European Application No. EP20170739061, dated Jan. 2, 2024, 4 pages.

\* cited by examiner

COMPOSITIONS AND METHODS FOR PROTEIN ELECTROPHORESIS

CROSS-REFERENCE TO RELATED APPLICATION

This application is a continuation of U.S. patent application Ser. No. 16/549,946, filed Aug. 23, 2019, which claims priority to and the benefit of U.S. Provisional Application No. 62/722,017, filed Aug. 23, 2018, and U.S. Provisional Application No. 62/797,127, filed on Jan. 25, 2019, the contents of which are hereby incorporated by reference in their entireties.

FIELD

The invention relates generally to protein electrophoresis. More particularly, the invention relates to solutions suitable for use in protein capillary electrophoresis, e.g., with sodium dodecylsuflate or related compositions and methods.

BACKGROUND

Electrophoresis may be used to separating mixture of molecules based on their different rates of travel in electric fields. Generally, electrophoresis refers to the movement of suspended or dissolved molecules through a fluid or gel under the action of an electromotive force applied to one or more electrodes or electrically conductive members in contact with the fluid or gel. Some known modes of electrophoretic separation include separating molecules based, at least in part, on differences in their mobilities in a buffer solution (commonly referred to as zone electrophoresis), in a gel or polymer solution (commonly referred to as gel electrophoresis), or in a potential of hydrogen (pH) gradient (commonly referred to as isoelectric focusing). In some instances, biomolecule separation can be carried out in a capillary tube by capillary electrophoresis. U.S. patent application Ser. No. 16/033,808, entitled "System and Methods for Capillary Electrophoresis, Isoelectric Point, and Molecular Weight Analysis," the disclosure of which is hereby incorporated by reference in its entirety, describes various systems, methods, and techniques for carrying out capillary electrophoresis.

Capillary Electrophoresis-sodium dodecyl sulfate (CE-SDS) is used, for example, for size-based characterization and purity analysis of proteins including monoclonal antibodies (mAbs) and biologic drugs.

SUMMARY

CE-SDS sample preparation generally requires heating a sample containing an analyte diluted in an appropriate loading buffer containing SDS and optionally either a reducing agent for reduced (R) analysis or an alkylating agent for non-reduced (NR) analysis. Fragmentation of proteins is a concern in preparation and analysis of biomolecules. The heating step has been observed to cause fragment of some analytes, including proteins such as mAbs. This fragmentation is particularly problematic in CE-SDS-NR. The problem has remained unsolved in the industry for some time.

Applicant has developed low-fragmentation loading buffers. Advantageously, the disclosed sample loading buffers and methods of use thereof may be used in CE-SDS.

In one aspect, the disclosure provides sample loading buffers. In another aspect, the disclosure provides methods for capillary electrophoresis. In some embodiments, the methods comprise providing an analyte with one or more polypeptides or a solution comprising such an analyte; contacting the analyte or solution with a sample loading buffer, thereby generating a sample; loading the sample onto a capillary; applying a voltage across the capillary to resolve the one or more polypeptides; and detecting the one or more polypeptides.

In some embodiments, the sample loading buffers comprise an acidic buffer and a basic buffer. The acidic buffer may be MES, MOPS, MOPSO, and ACES. The basic buffer may be Arginine and BTP. In certain embodiments, the pH of the loading buffer is between about 6.0 to about 7.6. In other embodiments, the pH of the loading buffer is between about 7.0 to about 7.4.

Advantageously, the compositions and methods of the disclosure provide for low fragmentation, better sample injection efficiency, better sensitivity, similar or better peak profiles for internal standards or analytes, and/or fewer separation aberrations compare to other sample buffers.

Other embodiments are provided in the Detailed Description that follows. The invention is limited solely by the claims.

BRIEF DESCRIPTION OF THE DRAWINGS

FIG. 5A shows comparison of the final buffer candidate to PS SB using Bio-Techne® recombinant adalimumab. In zoomed chromatogram (FIG. 5B), no changes in peak shape of IS are observed.

FIG. 8A shows trastuzumab biosimilar; zoomed in FIG. 8B.

FIG. 9A shows rituximab biosimilar; zoomed in FIG. 9B.

FIG. 10A shows bevacizumab biosimilar; zoomed in FIG. 10B.

FIG. 11A shows golimumab biosimilar; zoomed in FIG. 11B.

FIG. 12A shows the full chromatogram;

FIG. 12B is zoomed image.

DETAILED DESCRIPTION

Figure 1A:
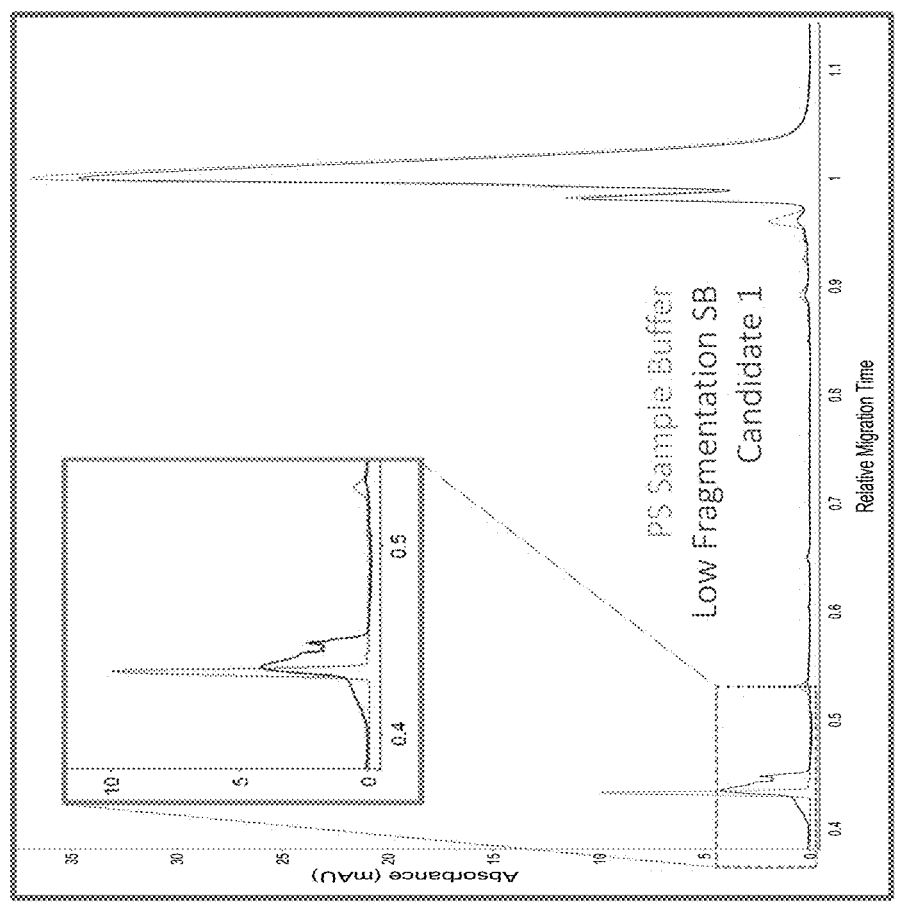
FIGS. 1A-1E depict development of a sample loading buffer. Negative effect on peak profile and resolution were observed in an initial sample buffer of 50 mM MES-Tris pH 6.5 (Candidate 1), including poorly resolved internal standard (IS) (FIG. 1A). Comparison to 50 mM MES/MES base pH 6.5 and ProteinSimple® Sample Buffer (Maurice CE-SDS 1X Sample Buffer) (PS_SB) is shown in FIG. 1B; zoomed in FIG. 1C. Dilution of rituximab in sample buffer candidate 2, 50 mM MOPSO-BTP, results in decreased resolution (FIG. 1D). Comparison of candidate 2 to ProteinSimple® Sample Buffer (PSSB) as well as other buffers is shown in FIG. 1E.
Figure 1B:
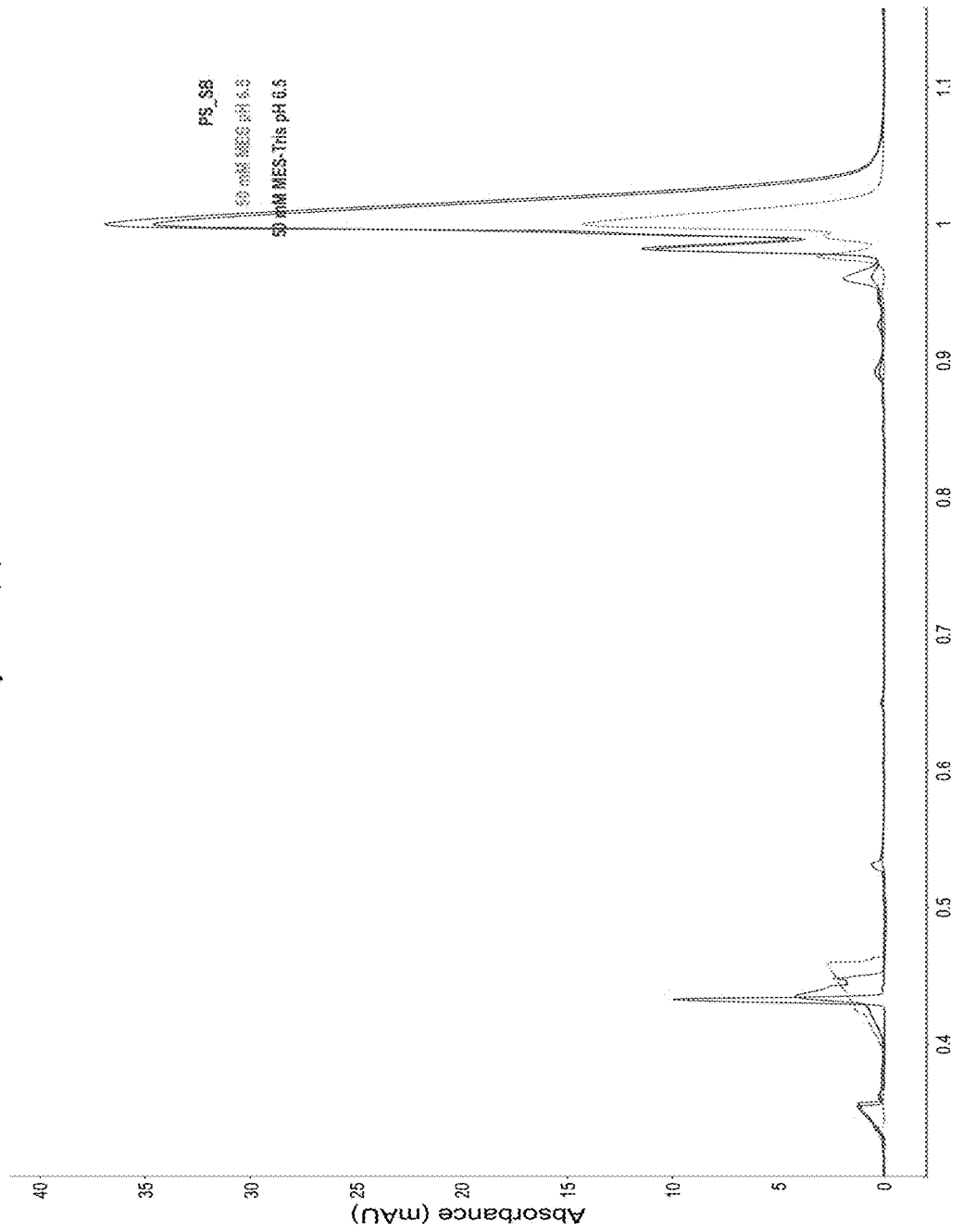
Figure 1C:
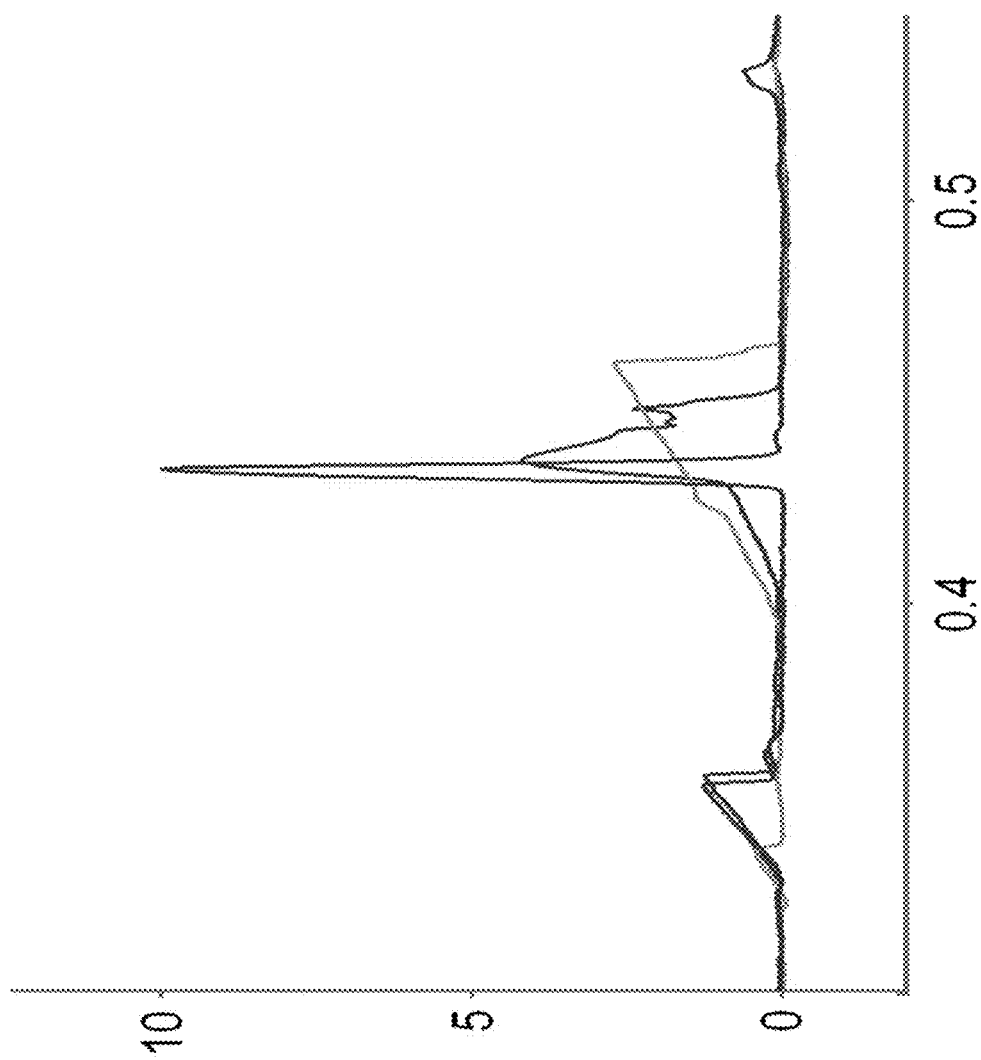
Figure 1D:
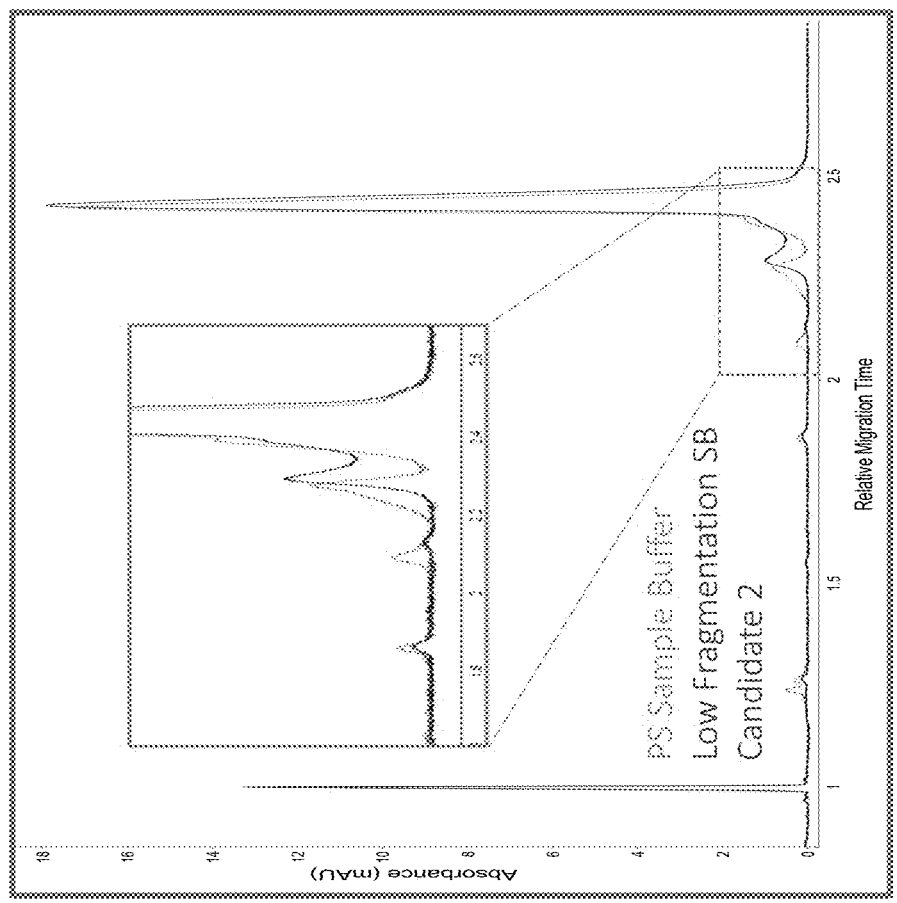
Figure 1E:
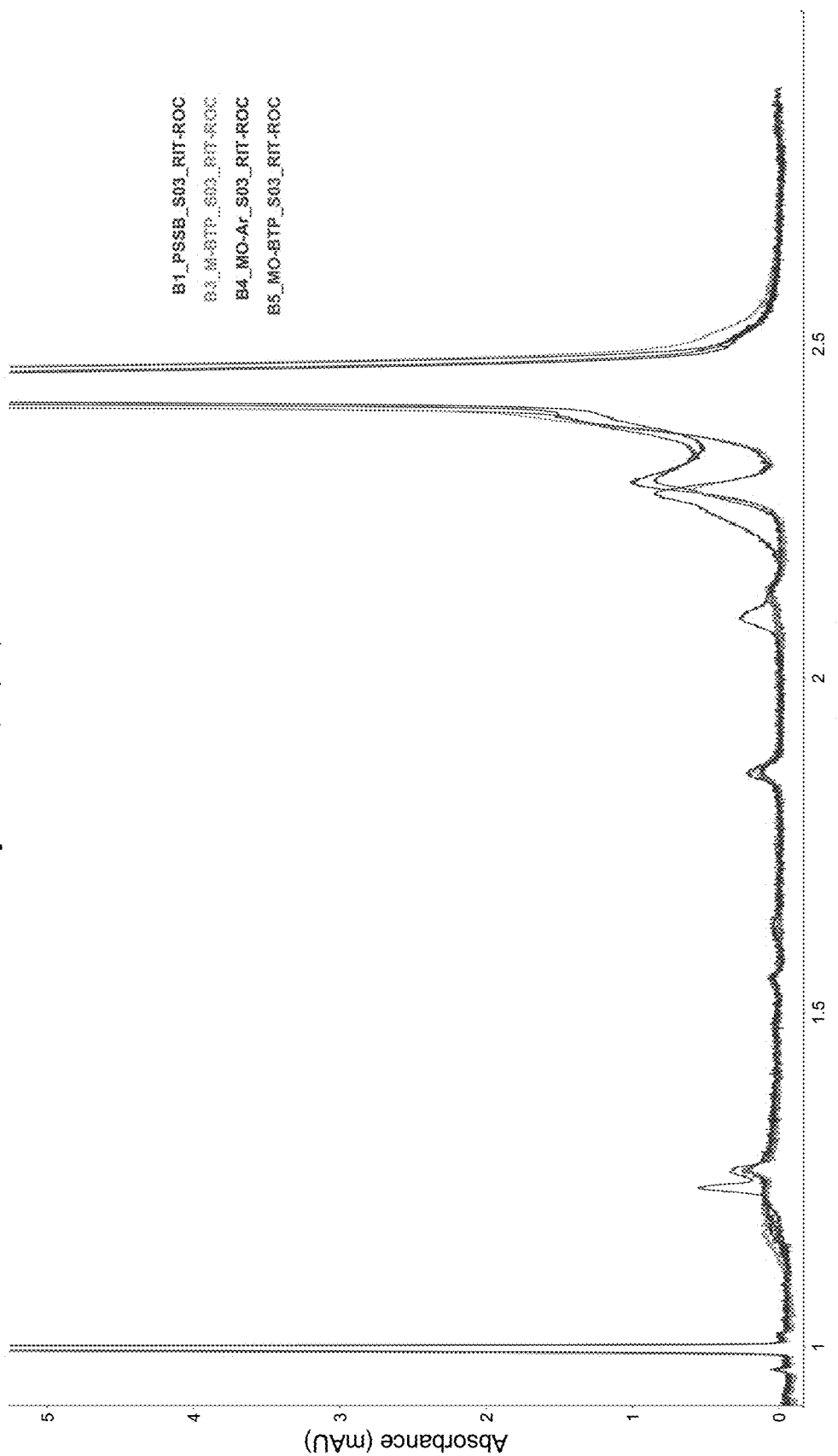
Figure 2:
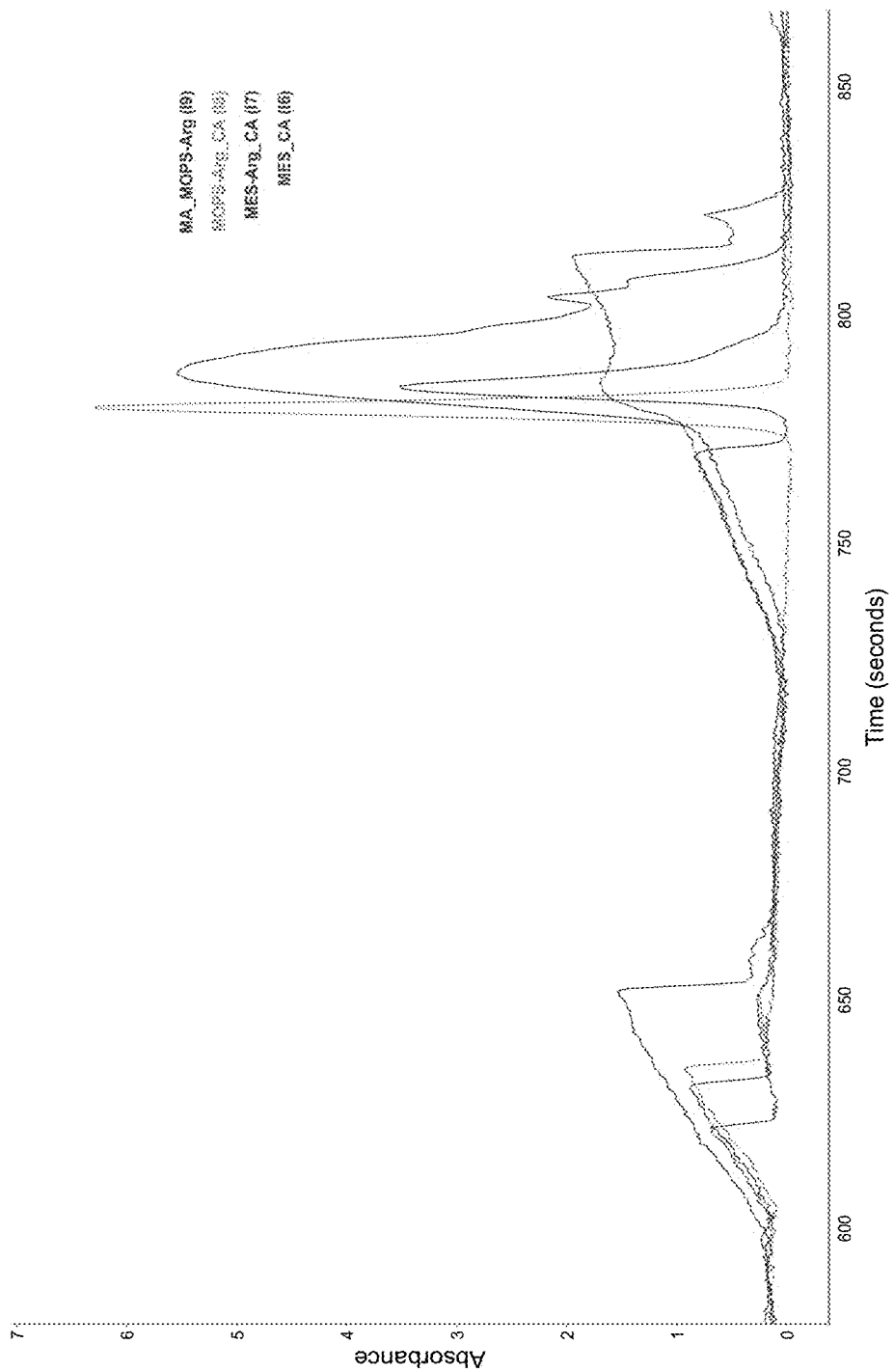
FIG. 2 shows CE-SDS performed in various buffer systems labeled by injection number (I6, I7, I8, I9). Abbreviations are as follows: MA_MOPS-Arg, MOPS-Arg buffer system; MOPS-Arg_CA (citric acid), MOPS-Arg buffer system; MES-Arg_CA (citric acid), MES-Arg buffer system; MES-CA (citric acid), MES-MES base buffer system.
Figure 3A:
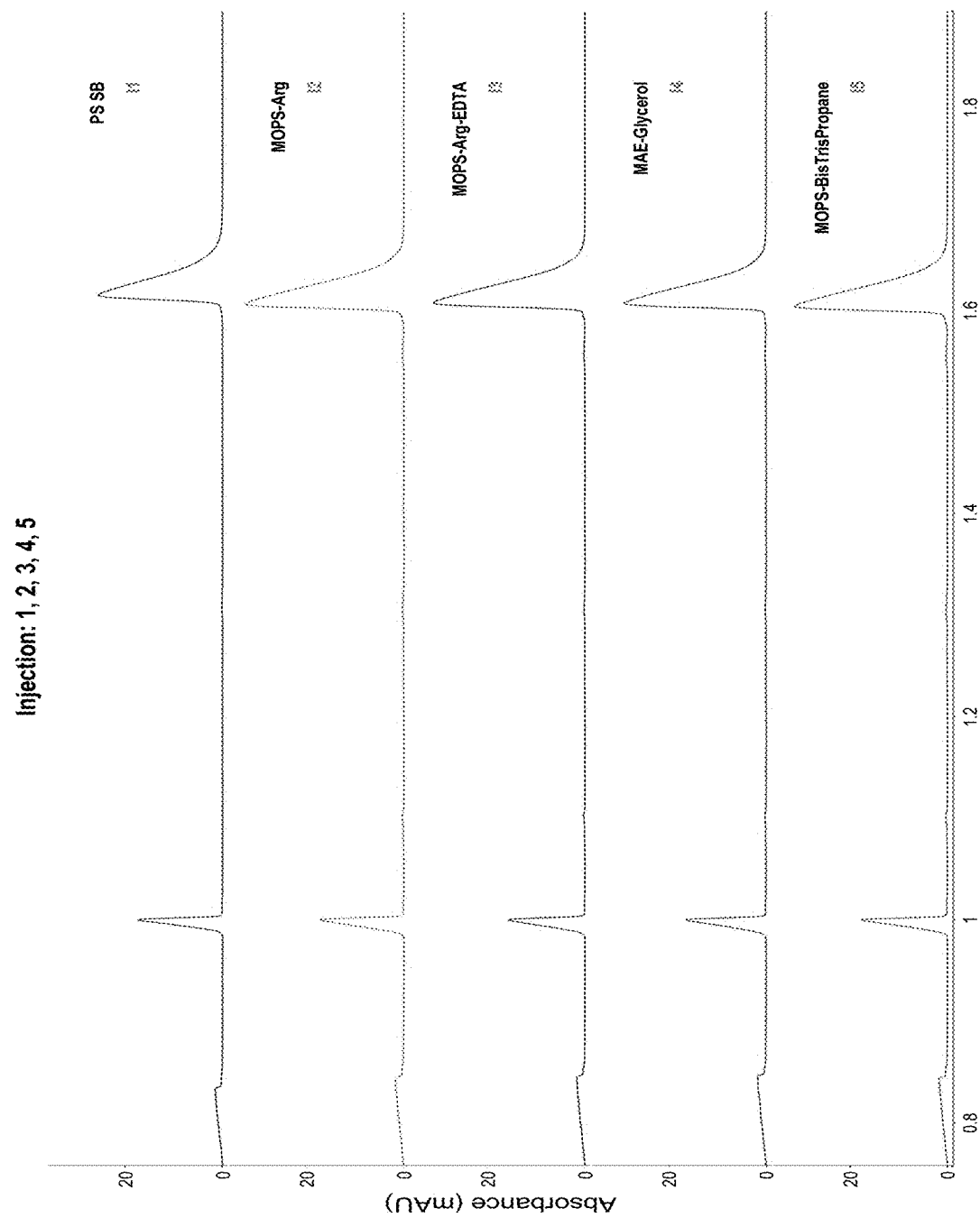
FIGS. 3A-3B show CE-SDS performed in various buffer systems labeled by injection number I1, I2, I3, I4, or I5 (FIG. 3A) and I7, I8, or I9 (FIG. 3B). Abbreviations not defined in the detailed description are as follows: PS SB, ProteinSimple® Sample Buffer (Maurice CE-SDS 1X Sample Buffer), MAE-Glycerol, MOPS-Arg EDTA glycerol.
Figure 3B:
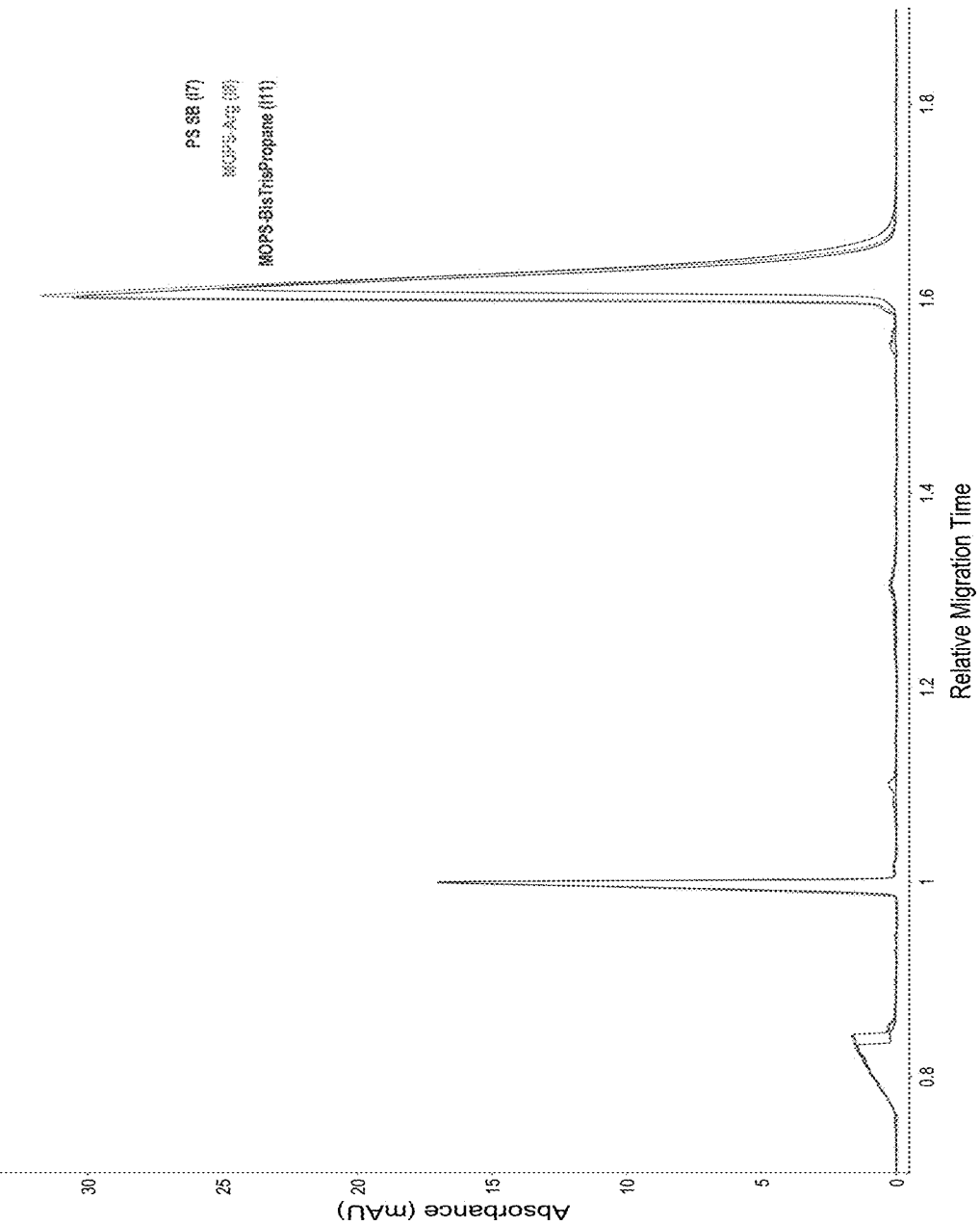

Compositions and methods for performing capillary electrophoresis are described herein. In various embodiments, the compositions and methods of the disclosure provide for low fragmentation, better sample injection efficiency, better sensitivity, similar or better peak profiles for internal standards or analytes, and/or fewer separation aberrations compared to other sample buffers.

As used in this specification, the singular forms "a," "an" and "the" include plural referents unless the context clearly dictates otherwise. Thus, for example, the term "a polypeptide" is intended to mean a single polypeptide or a mixture of polypeptides.

As used herein, the terms "about" and "approximately" generally mean plus or minus 10% of the value stated. For example, about 0.5 would include 0.45 and 0.55, about 10 would include 9 to 11, about 1000 would include 900 to 1100. As PH is logarithmic, "about" applied to pH generally means plus or minus 0.1 of the value stated. For example, pH 7.0 would include 6.9 to 7.1.

As used herein, the terms "analyte" and/or "target analyte" refer to any molecule or compound to be separated and/or detected with the methods, apparatus and systems provided herein. Suitable analytes include, but are not limited to, small chemical molecules such as, for example, environmental molecules, clinical molecules, chemicals, pollutants, and/or biomolecules. More specifically, such chemical molecules can include, but are not limited to pesticides, insecticides, toxins, therapeutic and/or abused drugs, antibiotics, organic materials, hormones, antibodies, antibody fragments, antibody-molecule conjugates (e.g., antibody-drug conjugates), antigens, cellular membrane antigen, proteins (e.g., enzymes, immunoglobulins, and/or glycoproteins), nucleic acids (e.g., DNA and/or RNA), lipids, lectins, carbohydrates, whole cells (e.g., prokaryotic cells such as pathogenic bacteria and/or eukaryotic cells such as mammalian tumor cells), viruses, spores, polysaccharides, glycoproteins, metabolites, cofactors, nucleotides, polynucleotides (comprising ribonucleic acid and/or deoxyribonucleic acid), transition state analogs, inhibitors, receptors, receptor ligands (e.g., neural receptors or their ligands, hormonal receptors or their ligands, nutrient receptors or their ligands, and/or cell surface receptors or their ligands), receptor-ligand complexes, nutrients, electrolytes, growth factors and other biomolecules and/or non-biomolecules, as well as fragments and combinations thereof. In some embodiments, the analyte is a protein or a protein complex, and the sample is a cellular lysate or a purified protein. Other suitable analytes can include aggregates, agglomerates, floc, and/or dispersed phase droplets or particles of colloids and/or emulsions.

As used herein, the term "sample" refers to a composition that contains an analyte or analytes to be detected. A sample, in some embodiments, is heterogeneous, containing a variety of components (e.g., different proteins) or homogenous, containing one component (e.g., a population of one protein). In some instances, a sample can be naturally occurring, a biological material, and/or a manufactured material. Furthermore, a sample can be in a native (e.g., a cell suspension) or denatured form (e.g., a lysate). In some instances, a sample can be a single cell (or contents of a single cell, e.g., as a cellular lysate from the single cell, or a purified protein) or multiple cells (or contents of multiple cells, e.g., as a cellular lysate from the multiple cells, or a purified protein from the multiple cells), a blood sample, a tissue sample, a skin sample, a urine sample, a water sample, and/or a soil sample. In some instances, a sample can be from a living organism, such as a eukaryote, prokaryote, mammal, human, yeast, and/or bacterium or the sample can be from a virus.

In some embodiments, the sample is a heterogeneous biological sample or derived from a heterogeneous biological sample, for example a tissue lysate, a cellular lysate or a mixture of biomolecules such as proteins (e.g., a purified protein). In a further embodiment, a protein within the cellular lysate is the analyte to be detected by the methods and systems described herein. In a further embodiment, the apparatus, systems, and methods provided herein provide for the detection of a particular form of a protein, for example, a phosphorylated protein. The cellular lysate, for example, can be the lysate of one cell or a mixture of cells. Moreover, the cellular lysate can include a single cell type, or multiple cell types. The cell type, in some embodiments, includes a stem cell or a cancer cell, or a population of stem cells, or a population of cancer cells. In some embodiments, a sample comprises one or more stem cells (e.g., any cell that has the ability to divide for indefinite time periods and to give rise to specialized cells). Suitable examples of stem cells can include but are not limited to embryonic stem cells (e.g., human embryonic stem cells (hES)), and non-embryonic stems cells (e.g., mesenchymal, hematopoietic, induced pluripotent stem cells (iPS cells), or adult stem cells (MSC)).

In some instances, prior to detecting an analyte in a sample with the apparatus and systems provided herein, processing may be performed on the sample. For example, a sample can be subjected to a lysing step, denaturation step, heating step, purification step (e.g., protein purification), precipitation step, immunoprecipitation step, column chromatography step, centrifugation, etc. In some embodiments, a sample is subjected to a denaturation step prior detecting and/or separating a target analyte in a sample with the methods, apparatus, and systems described herein. The processing step on the sample, in some embodiments, is performed in one of the apparatus or systems described herein. In another embodiment, the processing step is performed prior to introducing the sample into one of the apparatus or systems set forth herein.

As used herein, the terms "standard" and/or "internal standard" refer to a well-characterized substance of known amount and/or identity (e.g., known isoelectric point, molecular weight, electrophoretic mobility profile, number of base pairs in the case of a nucleic acid, molecular composition, etc.) that can be added to a sample comprising the analyte, for comparative purposes. In some embodiments, a known quantity of standard is added to a sample comprising one or more analytes, and both the standard and the molecules in the sample, including the analyte(s) are separated on the basis of isoelectric point by electrophoresis). A comparison of the standard and analyte signal then provides a quantitative or semi-quantitative measure of the amount of analyte originally present in the sample.

Molecular weight standards are known. In some instances, the standard and/or the analyte(s) can be detected with one or more detection molecules or reagents, such as with an antibody against the analyte or a labeling moiety attached to the standard. In some embodiments, a primary antibody is used to bind the target analyte, and a secondary antibody conjugated to a fluorescent or a chemiluminescent reagent is introduced to bind the primary antibody or the primary antibody-analyte complex. The signal of the fluorescent or chemiluminescent molecule is then detected. In other instances, the standard and/or the analyte(s) can be detected via native fluorescence (e.g., via fluorescence of tryptophan amino acids within the standard and/or analyte(s)) and/or absorbance.

The signal of the standard and the signal of the analyte(s) can then be compared to measure the concentration of the analyte(s) in the sample. In addition or alternatively, a relevant characteristic of the analyte (e.g., isoelectric point, molecular weight, etc.) can be determined by comparison to the standard.

In some embodiments, an internal standard can be a purified form of the analyte itself, which is generally made distinguishable from the analyte in some way. Any method of obtaining a purified form of the analyte can include but is not limited to purification from nature, purification from organisms grown in the laboratory (e.g., via chemical synthesis), and/or the like. The distinguishing characteristic of an internal standard can be any suitable change that can include but is not limited to dye labeling, radiolabeling, or modifying the mobility of the standard during the electrophoretic separation so that it is distinguishable from the analyte. For example, the analyte and the internal standard can each be labeled with fluorescent dyes that are each detectable at discrete emission wavelengths, thereby allowing the analyte and the standard to be independently detectable. In some instances, an internal standard is different from the analyte but behaves in a way similar to or the same as the analyte, enabling relevant comparative measurements. In some embodiments, a standard that is suitable for use can be any of those described in U.S. Patent Application Publication No. 2007/0062813 entitled, "Electrophoresis Standards, Methods and Kits," filed on Sep. 20, 2006, the disclosure of which is incorporated herein by reference in its entirety.

In some instances, multiple analytes are detected and characterized from a single sample in a single capillary tube by the apparatus, systems, and methods provided herein. For example, in some embodiments, the multiple analytes are a population of proteins or a subpopulation of proteins. In this regard, it may not be practical to include a single internal standard corresponding to each of the individual proteins of the population of proteins or subpopulation of proteins.

Analytes and/or standards described above, in some embodiments, are separated by any suitable mobility parameter such as charge, molecular weight, electrophoretic mobility (e.g., influenced by molecular weight, characteristic length, area, or volume, oligonucleotide length, or other suitable characteristic), and/or the like. For example, in some embodiments, a sample is subjected to an electrophoretic separation in a capillary tube comprising a separation matrix, based on a mobility parameter such as an isoelectric point or the like. The capillary tube can include a separation matrix, which can be added in an automated fashion. The separation matrix, in some embodiments, is an isoelectric separation matrix, and has similar or substantially the same properties of a polymeric gel, used in conventional electrophoresis experiments, such as a pH gradient. Capillary electrophoresis in the separation matrix is analogous to separation in a polymeric gel, such as a polyacrylamide gel or an agarose gel, where molecules are separated on the basis of the mobility parameter of the molecules in the sample, by providing a porous passageway through which the molecules can travel.

In some embodiments, once the separation is complete, the components of the separated sample (e.g., including the analytes and/or standards) can be immobilized to a wall(s) of the capillary using any suitable method including but not limited to chemical, photochemical, and heat treatment. In some embodiments, the components of the separated sample are immobilized in a fluid path (e.g., defined by a capillary or the like) after the molecules have been separated by electrophoresis. For example, in some embodiments, immobilization occurs by subjecting the separated sample and the capillaries to ultraviolet (UV) light, which serves to immobilize the analyte(s) (if present in the sample) and molecules in the sample to the walls of the capillary. The immobilization can be via covalent bonds or non-covalent means such as by hydrophobic or ionic interaction. In another embodiment, a reactive moiety can be used to covalently immobilize the resolved analyte or analytes in the fluid path. The reactive moiety can be attached directly or indirectly to the fluid path (e.g., on the wall(s) of the capillary tube). In some embodiments, the reactive moiety can be supplied in solution or suspension, and can be configured to form bridges between the wall of the fluid path and the molecules in the sample upon activation. The reactive moiety can line the fluid path or can be present on a linear or cross-linked polymer in the fluid path, which may or may not be linked to the wall of the fluid path before and/or after activation. The reactive moiety can be and/or can include any reactive group that is capable of forming a covalent linkage with a corresponding reactive group of individual molecules of the sample such as, for example, those described above.

In some embodiments, the reactive moiety comprises a functional group that can be converted to a functionality that adheres to an analyte via hydrophobic interactions, ionic interactions, hydrogen bonding etc. In some embodiments, such reactive moieties can be activated by the UV light, laser, temperature, or any other source of energy in order to immobilize the analytes onto the surfaces of the fluid paths and/or onto the surfaces of particles attached to the surfaces of fluid paths. In some embodiments, the surfaces of the fluid paths are functionalized with thermally responsive polymers that enable changes in hydrophobicity of the surfaces upon changing the temperature. In some embodiments, the analytes are immobilized on such surfaces by increasing hydrophobicity of a temperature responding polymer when a certain temperature is reached within the fluid path. In yet other embodiments, the analyte can be probed for, and/or detected without first being immobilized onto the surfaces of the fluid paths. By way of example, the analytes can be separated based on an isoelectric point (e.g., via isoelectric focusing) and maintained at their respective isoelectric points for at least as long as the sample within the fluid path is subjected to an electric current. In other words, once the analytes and/or standards are separated, the apparatus and/or systems described herein can continue to provide a flow of electric current operable to maintain the analytes and/or standards at their respective isoelectric points (e.g., immobilization).

Immobilized and/or otherwise separated analytes and/or standards are then probed for, and detected with one or more detection agents. A detection agent is capable of binding to or interacting with the analyte and/or standard to be detected. Detection agents allow the detection of a standard and an analyte by any means such as but not limited to fluorescent dye(s), optical dye(s), chemiluminescent reagent(s), radioactivity, particles, magnetic particle(s), paramagnetic particle(s), etc. Detection agents can include any organic or inorganic molecules such as, for example, proteins, peptides, antibodies, enzyme substrates, transition state analogs, cofactors, nucleotides, polynucleotides, aptamers, lectins, small molecules, ligands, inhibitors, drugs, and other biomolecules as well as non-biomolecules capable of binding the analyte to be detected. In some embodiments, the detection agents comprise one or more label moieties (as described above). In some embodiments, the detection agents comprise one or more label moiety(ies). In embodiments employing two or more label moieties, each label moiety can be the same, or some, or all, of the label moieties may differ.

In some embodiments, the detection agent is used as a secondary reagent. For example, in some embodiments, the detection agent is designed to bind a first molecule that is introduced to bind to the analyte and/or standard, or the complex of the first molecule with the analyte and/or standard. For example, in some embodiments, a "primary" monoclonal or polyclonal antibody is first introduced into the capillary tube comprising the immobilized sample. This "primary" antibody binds to the analyte of interest (if present in the sample) and unbound primary antibodies are washed away. Next, a "secondary" antibody is introduced, which is designed to bind either the primary antibody, or a region spanning the primary antibody-analyte complex. The secondary antibody includes a label moiety for detecting and/or visualizing the presence/absence of the analyte of interest.

In some embodiments, a multiplex immunoassay is carried out in the apparatus and systems provided herein, to detect the presence or absence of two or more analytes of interest (for example, two, three, four or five analytes) in the sample, or to quantify the amount of two or more analytes in the sample. In a further embodiment, the detection agent is the same for each of the analytes of interest. For example, the detection agent for each analyte is a secondary antibody conjugated to a chemiluminescent label such as horseradish peroxidase. Differentiation between the analytes occurs by initially introducing distinct primary antibodies into the capillary tube, where each primary antibody is specific for a unique analyte of interest.

The label moiety, conjugated to the secondary antibody, can be any suitable label. For example, general labels can include optical dyes (e.g., colored or fluorescent dyes); chemiluminescent labels, phosphorescent labels, enzymatic labels (e.g., alkaline phosphatase and/or horseradish peroxidase), bioluminescent labels, isotopic labels (e.g., radioactive isotopes or heavy isotopes), mass labels, and/or particle labels (e.g., colloids, magnetic particles, etc.). In some embodiments, the label moiety is a chemiluminescent moiety. In a further embodiment, the chemiluminescent moiety is horseradish peroxidase (HRP). In some embodiments, the HRP is conjugated to a secondary antibody, and is used in an immunoassay to detect an analyte or a plurality of analytes in a sample. In some embodiments, a label moiety can be a single isomer dye. In some embodiments, the label moiety can be a fluorescent dye that can include any entity that provides a fluorescent signal. For example, a fluorescent dye can include a resonance-delocalized system or aromatic ring system that absorbs light at a first wavelength and emits fluorescent light at a second wavelength in response to the absorption event. A fluorescent dye can be any of a variety of classes of fluorescent compounds, for example, xanthenes, rhodamines, fluoresceins, cyanines, phthalocyanines, squaraines, bodipy dyes, coumarins, oxazines, and carbopyronines. In some embodiments, the fluorescent dye is 5-carboxytetramethylrhodamine (5-TAMRA), and/or any other suitable class of fluorescent compound.

In some embodiments, the label moiety can be and/or can include a chemiluminescent label. Suitable labels moieties can include enzymes capable of reacting with a chemiluminescent substrate in such a way that photon emission by chemiluminescence is induced. For example, enzymes can induce chemiluminescence in other molecules through enzymatic activity. Such enzymes can be and/or can include peroxidase, for example, horseradish peroxidase (HRP), β-galactosidase, phosphatase, etc. In some embodiments, the chemiluminescent label can be selected from any of a variety of classes of luminol label, an isoluminol label, etc. In some embodiments, a detection agent can include chemiluminescent-labeled antibodies, for example, a secondary antibody covalently bound to HRP. In some embodiments, the detection agents comprise chemiluminescent substrates such as, for example, Galacton substrate available from Applied Biosystems of Foster City, Calif. or SuperSignal West Femto Maximum Sensitivity substrate available from Pierce Biotechnology, Inc. of Rockford, Ill., or any other suitable substrates. In some embodiments, a detection agent can be any of those described in U.S. Pat. Nos. 6,689,576, 6,395,503, 6,087,188, 6,287,767, 6,165,800, and 6, 126,870, the disclosures of which are incorporated herein by reference in their entireties.

In some embodiments, the label moiety can be and/or can include a bioluminescent compound (e.g., found in biological systems in which a catalytic protein increases the efficiency of the chemiluminescent reaction). The presence of a bioluminescent compound is determined by detecting the presence of luminescence. Suitable bioluminescent compounds include, but are not limited to luciferin, luciferase, and aequorin.

In some embodiments, the label moiety can be and/or can include a fluorescent dye. Such fluorescent dyes can include a resonance-delocalized system or aromatic ring system that absorbs light at a first wavelength and emits fluorescent light at a second wavelength in response to the absorption event. Fluorescent dyes can be any of a variety of classes of fluorescent compounds such as but not limited to xanthenes, rhodamines, fluoresceins, cyanines, phthalocyanines, squaraines, bodipy dyes, coumarins, oxazines, and carbopyronines. In some embodiments, for example, where detection agents contain fluorophores, such as fluorescent dyes, their fluorescence is detected by exciting them with an appropriate light source, and monitoring their fluorescence by a detector sensitive to their characteristic fluorescence emission wavelength.

As provided above, in some embodiments, two or more different agents can be used to bind to or interact with two or more different analytes to enable more than one type of analytes to be detected simultaneously. In some embodiments, two or more different detection agents, which bind to or interact with the one analyte, can be detected simultaneously. In various embodiments, using two or more different detection agents, one agent, for example a first primary antibody, can bind to or interact with one or more analytes to form a first agent-analyte complex, and a second reagent, the detection agent, for example a secondary antibody, can be used to bind to or interact with the first agent-analyte complex.

In another embodiment, two different detection agents, for example antibodies for both phospho- and non-phospho- forms of analyte of interest can enable detection of both forms of the analyte of interest. In some embodiments, a single specific detection agent, for example an antibody, can allow detection and analysis of both phosphorylated and non-phosphorylated forms of an analyte. In some embodiments, multiple detection agents can be used with multiple substrates to provide color multiplexing. For example, different chemiluminescent substrates can be used to emit photons of differing color. Selective detection of different colors (e.g., via a diffraction grating, a prism(s), a series of colored filters, and/or the like) can allow determination of which color photons are being emitted at any position along a fluid path (e.g., along a molecular weight gradient), and therefore determination of which detection agents are present at each emitting location. In some embodiments, different chemiluminescent reagents can be supplied sequentially, allowing different bound detection agents to be detected sequentially.

In general, during the standard immunoassay process carried out in the apparatus and systems described herein, a portion of the internal standard will be lost due to the various wash processes. Thus, it is generally desirable to load a sufficient amount of internal standard in the sample at the beginning of the assay so that enough signal can be generated by the internal standard that remains in the capillary after the immunoassay to provide coordination to calibrate the curve and analyze the molecular weight and/or identity (e.g., amino acid number or number of oligonucleotide base pairs) of the analyte. A relatively large amount of internal standard, however, may interfere with the capture of the analyte if the standard and the analyte are located in the same position. As such, some standards do not locate with the analyte during and/or at the end of the electrophoresis. Such a standard, however, may not produce a reliable calibration curve for the detection of the analyte. Therefore, in some embodiments, a sample can include more than one standard. For example, an internal standard can be formed by and/or include a first standard (referred to as a "bright standard" or a "registration standard") and a second standard (referred to as a "dim standard"). The bright standard can be a standard that has characteristics (such as an isoelectric point) that differs from that of the analyte. As such, after electrophoresis, the location of registration standard and the analyte are located apart from each other in the capillary. Thus, the fluorescence emitted from the bright standard and the analyte will not overlap and interfere with each other. The dim standard can be a standard that has characteristics (such as an isoelectric point) that are similar to that of the analyte. As such, after electrophoresis, the location of the registration standard and the analyte are located close to each other in the capillary.

The bright standard can locate at a position along a flow path (e.g., defined by a capillary or the like) that is different from the position of the analyte and provides a coordinate (e.g., an anchor point) for the dim standard to locate close to or at the same position as the analyte, thereby providing an accurate calibration curve. Generally, the bright standard produces a fluorescence that is brighter than the fluorescence emitted by the dim standard after the internal standard and the analyte have been separated. The difference of the brightness between the bright standard and dim standard can be attributed to the difference in the nature of emission and/or to the difference in the amounts of the two standards contained in the internal standard. For example, a large quantity of bright standard and a small quantity of dim standard can be mixed to form a standard that can produce a "bright" signal from the bright standard and a "dim" signal from the dim standard. Thus, a "bright" signal due to the bright standard and a "dim" signal due to the dim signal are detected after the separation step by electrophoresis. In some embodiments, an internal standard can include a bright standard and a dim standard such as, for example, those described in U.S. Patent Application Publication No. 2011/0011740, the disclosure of which is incorporated herein by reference in its entirety.

The embodiments described herein can be used to facilitate one or more analyses (e.g., via molecular weight analysis and/or isoelectric focusing) of one or more analytes in a single system followed by visualization and detection analytes within a sample. Embodiments described herein can provide the functionality of pipettes and microfluidic paths, thereby enabling the analysis of very small volume samples. Such apparatus and/or systems can include any suitable device, mechanism, assembly, subassembly, electronic device, actuator, and/or the like that can enable the apparatus and/or system to, for example, separate, immobilize, and/or detect any suitable target analytes. More specifically, the apparatus and systems described herein are configured to receive a cartridge including one or more capillaries and to expose at least a portion of the cartridge to negative pressure differential (e.g., produced by a vacuum source) operable to draw a volume of fluid (e.g., one or more reagents, samples, buffers, washes, detectors, analytes, ampholytes, and/or the like) from one or more wells or trays included in the apparatus and/or system into the capillary(ies) of the cartridge.

In some embodiments, such a cartridge can have at least one capillary that is fixedly coupled to a cartridge body. The capillary(ies) (referred to henceforth in the singular, for simplicity) are configured to be placed in fluid communication with one or more fluid reservoirs (e.g., disposed in the cartridge body and/or disposed in or defined by a reagent tray or the like). In some embodiments, the one or more fluid reservoirs can be wells or the like containing a fluid with constituents having any of the chemistries described above. In some embodiments, at least a part of the cartridge can be electrically conductive (e.g., formed from copper, platinum, stainless steel, electrically conductive microplate plastic, carbon-infused plastic, an electrically conductive polymer, and/or any other suitable material). In some embodiments, such portions of the cartridge can have a volume resistivity of less than 25 ohm*centimeters (ohm·cm) and a surface resistivity of 1000 ohms (or 1 kilo-ohm (k$\Omega$)) to 100 k$\Omega$. In other embodiments, the cartridge and/or portions thereof is/are substantially nonconductive.

The capillary of the cartridge defines a lumen that receives at least a portion of a sample, solution, reagent, analyte, and/or any other suitable fluid or gel. The capillary can be any suitable shape, size, or configuration and can be formed from any suitable material (e.g., glass, plastic, silicon, fused silica, gel, PYREX™ (amorphous glass), and/or the like) that allows a liquid and/or dissolved molecules to flow through the lumen. For example, in some embodiments, the length of the capillary can be based at least in part on factors such as sample size or volume and the extent of sample separation when resolving the analyte or analytes of interest (e.g., between about 2 centimeters (cm) and about 20 cm), where a longer capillary can result in increased separation of samples, which in turn, can improve resolution of complex mixtures and/or mixtures having a low abundance of analytes. In some embodiments, the capillary of a cartridge can be an elongate member having a rounded or circular cross-sectional shape or a polygonal cross-sectional shape (e.g., trapezoidal, rectangular, square, pentagonal, octagonal, etc.). In some embodiments, the shape and/or size of the lumen defined by the capillary can be based at least in part on the sample, the sample volume, and/or the type of analysis (e.g., with an inner diameter of about 10 micrometers or "microns" (μm) to about 1000 μm). For example, a capillary having a relatively small inner diameter can be associated with and/or otherwise used for relatively low sample volumes, which can be suitable for expensive samples or reagents. Conversely, a capillary defining a relatively larger inner diameter can be associated with and/or otherwise used for relatively high sample volumes, which in some instances, can result in improved signal detection or the like. In other embodiments, the inner diameter can be based at least in part on the analysis to be performed (e.g., molecular weight-based separation, isoelectric focusing, etc.).

In some embodiments, the disclosure provides a sample loading buffer. In some embodiments, the sample loading buffer comprises a buffered aqueous solution comprising, consisting essentially of, or consisting of an acidic buffer selected from MES, MOPS, MOPSO, and ACES and a basic buffer selected from Arginine and BTP. Derivatives of the foregoing buffers may be employed. Selection and chemical synthesis of such derivatives are known in the art or within the skill of an ordinary artisan.

As used herein, "MES" refers to 2-(N-morpholino)ethanesulfonic acid. MES has a molecular weight of 195.2 and the chemical formula is $C_6H_{13}NO_4S$. Synonyms include: 2-morpholinoethanesulfonic acid; 2-(4-morpholino)ethanesulfonic acid; 2-(N-morpholino)ethanesulfonic acid; 2-(4-morpholino)ethanesulfonic acid; MES; MES hydrate; and morpholine-4-ethanesulfonic acid hydrate. MOPS is a similar pH buffering compound which contains a propanesulfonic moiety instead of an ethanesulfonic one. The chemical structure of MES is:

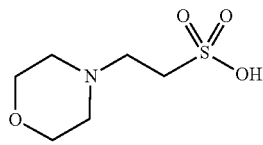 [SMILES: O=S(=O)(O)CCCN1CCOCC1]

As used herein, "MOPS" refers to 3-(N-morpholino) propanesulfonic acid. MOPS is a structural analog to MES. Its chemical structure contains a morpholine ring. HEPES is a similar pH buffering compound that contains a piperazine ring. With a pKa of 7.20, MOPS is an excellent buffer for many biological systems at near-neutral pH. The chemical structure of MOPS is:

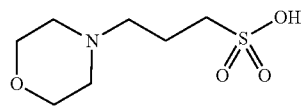 [SMILES: O=S(=O)(O)CCCCN1CCOCC1]

As used herein, "MOPSO" refers to 2-Hydroxy-3-morpholinopropanesulfonic acid. MOPSO and MOPS are chemically similar, differing only in the presence of a hydroxyl group on the C-2 of the propane moiety. MOPSO has a useful pH range of 6.5-7.9 in the physiological range. It has a pKa of 6.9 with ΔpKa/° C. of –0.015 and a solubility in water at 0° C. of 0.75 M. The chemical structure of MOPSO is:

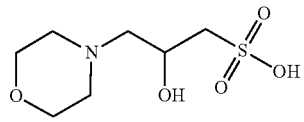 [SMILES: O=S(=O)(O)CCC(O)CN1CCOCC1]

As used herein, "ACES" refers to N-(2-Acetamido)-2-aminoethanesulfonic acid. ACES is a zwitterionic buffer with a useful buffering range of 6.1-7.5. The chemical structure of ACES is:

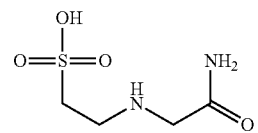 [SMILES: NC(=O)CNCCS(=O)(=O)O]

"Arginine" or "Arg" generally refers to L-arginine. It is should be understood, however, that the buffering property of arginine is not dependent, or only weakly dependent on chirality. In some embodiments, the sample loading buffer comprises R-arginine. It has a pKa of 12.5. The chemical structure of arginine is

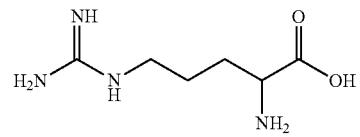

As used herein, "BTP" refers to Bis-Tris Propane, which is 1,3-bis(tris(hydroxymethyl) methylamino)propane. BTP is soluble in water; 15 g in 35 mL water (approximately 1.5 M) gives a clear colorless solution. The pH of a 1 M solution is between 10 and 12 at room temperature. BTP has a molecular weight of 282, a pKa1 of 6.8 at 25° C. and a pKa2 of 9.0 at 25° C. BTP is a buffer with an unusually wide buffering range, from approximately pH 6 to 9.5, due to its two pKa values being close in value. Because of the wide buffering range, particularly down to pH 6-7, this buffer has been used to enhance the stability or activity of restriction enzymes, compared to Tris buffer (which is a poor buffer below pH 7.5 and has a comparatively large change in pKa with temperature). BTP has the chemical structure:

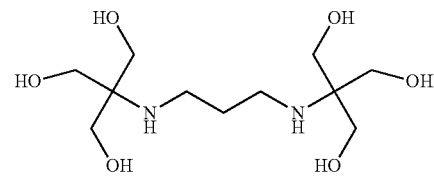 [SMILES: OCC(CO)(CO)NCCCNC(CO)(CO)CO]

In some embodiments, the sample buffer comprises an comprises, consists essentially of, or consist of a mixture of one, two, three, or four acidic buffers selected from MES, MOPS, MOPSO, and ACES, or derivatives thereof, and a basic buffer selected from Arginine and BTP. In some embodiments, the sample buffer comprises, consists essentially of, or consists of a mixture of at least one, two, three, four, or more acidic buffers selected from MES, MOPS, MOPSO, and ACES, or derivatives thereof, and at least one, two, or more basic buffers selected from Arginine and BTP, or derivatives thereof. In some embodiments, the sample buffer comprises an comprises, consists essentially of, or consists of a mixture of two, three, or four acidic buffers selected from MES, MOPS, MOPSO, and ACES, and either or both of Arginine and BTP.

In some embodiments, the sample loading buffer has a pH of about 3.5 to about 4.5, about 4.5 to about 5.5, about 5.5 to about 6.5, about 6.5 to about 7.5, or any range therebetween. In some embodiments, the sample loading buffer has a pH of about 6.0 to about 6.5, about 6.0 to about 6.7, about 6.0 to about 7.0, about 6.0 to about 7.3, about 6.0 to about 7.5, about 6.0 to about 7.7, about 6.0 to about 8.0, about 6.3 to about 6.5, about 6.3 to about 6.7, about 6.3 to about 7.0, about 6.3 to about 7.3, about 6.3 to about 7.5, about 6.3 to about 7.7, about 6.3 to about 8.0; about 6.5 to about 6.7, about 6.5 to about 7.0, about 6.5 to about 7.3, about 6.5 to about 7.5, about 6.5 to about 7.7, about 6.5 to about 8.0, about 6.7 to about 7.0, about 6.7 to about 7.3, about 6.7 to about 7.5, about 6.7 to about 7.7, about 6.7 to about 8.0, about 6.8 to about 7.2, about 7.0 to about 7.3, about 7.0 to about 7.5, about 7.0 to about 7.7, about 7.0 to about 8.0, about 7.3 to about 7.5, about 7.3 to about 7.7, about 7.3 to about 8.0, about 7.5 to about 7.7, about 7.5 to about 8.0, about 7.7 to about 8.0, or any range therebetween. In certain embodiments, the sample loading buffer has a pH of about 6.0 to about 7.6. In other embodiments, the sample loading buffer has a pH of about 7.0 to about 7.4.

In some embodiments, the sample loading buffer has a pH of about 3.5, about 4.0, about 4.5, about 5.0, about 5.5, about 6.0, about 6.5, about 7.0, or about 7.5. In other embodiments, the sample loading butter has a pH of about 6.0, about 6.2, about 6.4, about 6.6, about 6.8, about 7.0, about 7.2, about 7.4, about 7.6, about 7.8, or about 8.0.

In some embodiments, the sample loading buffer has a conductivity of 1.0 mS/cm or less, 1.5 mS/cm or less, 2.0 mS/cm or less, 2.5 mS/cm or less, 3.0 mS/cm or less, 3.5 mS/cm or less, 4.0 mS/cm or less, 4.5 mS/cm or less, 5.0 mS/cm or less, 5.5 mS/cm or less, 6.0 mS/cm or less, 6.5 mS/cm or less, 7.0 mS/cm or less, or 8.0 mS/cm or less. In some embodiments, the sample loading buffer has a conductivity of about 0 mS/cm to about 1.0 mS/cm, about 1.0 mS/cm to about 2.0 mS/cm, about 2.0 mS/cm to about 3.0 mS/cm, about 3.0 mS/cm to about 4.0 mS/cm, about 4.0 mS/cm to about 5.0 mS/cm, about 5.0 mS/cm to about 6.0 mS/cm, about 6.0 mS/cm to about 7.0 mS/cm, or about 7.0 mS/cm to about 8.0 mS/cm.

In some embodiments, the sample loading buffer comprises a buffered aqueous solution comprising, consisting essentially of, or consisting of a MES-Arginine buffer system.

In some embodiments, the sample loading buffer comprises a buffered aqueous solution comprising, consisting essentially of, or consisting of a MOPS-Arginine buffer system.

In some embodiments, the sample loading buffer comprises a buffered aqueous solution comprising, consisting essentially of, or consisting of a MOPSO-Arginine buffer system.

In some embodiments, the sample loading buffer comprises a buffered aqueous solution comprising, consisting essentially of, or consisting of an ACES-Arginine buffer system.

In some embodiments, the sample loading buffer comprises a buffered aqueous solution comprising, consisting essentially of, or consisting of a MES-BTP buffer system.

In some embodiments, the sample loading buffer comprises a buffered aqueous solution comprising, consisting essentially of, or consisting of a MOPS-BTP buffer system.

In some embodiments, the sample loading buffer comprises a buffered aqueous solution comprising, consisting essentially of, or consisting of a MOPSO-BTP buffer system.

In some embodiments, the sample loading buffer comprises a buffered aqueous solution comprising, consisting essentially of, or consisting of an ACES-BTP buffer system.

In some embodiments, the concentration of the acidic buffer is about 10 mM, about 20 mM, about 30 mM, about 40 mM, about 45 mM, about 50 mM, about 55 mM, about 60 mM, about 70 mM, about 80 mM, about 100 mM, or greater. In some embodiments, the concentration of the acidic buffer is about 20-30 mM, about 20-40 mM, about 20-50 mM, about 20-60 mM, about 20-70 mM, about 20-80 mM, about 30-40 mM, about 30-50 mM, about 30-60 mM, about 30-70 mM, about 30-80 mM, about 40-50 mM, about 40-60 mM, about 40-70 mM, about 40-80 mM, about 50-60 mM, about 50-70 mM, about 50-80 mM, about 60-70 mM, about 60-80 mM, or about 70-80 mM. In other embodiments, the concentration of the acidic buffer is about 40-45 mM, about 45-50 mM, about 50-55 mM, or about 55-60 mM.

In some embodiments, the concentration of MES is about 10 mM, about 20 mM, about 30 mM, about 40 mM, about 45 mM, about 50 mM, about 55 mM, about 60 mM, about 70 mM, about 80 mM, about 100 mM, or greater. In some embodiments, the concentration of MES is about 20-30 mM, about 20-40 mM, about 20-50 mM, about 20-60 mM, about 20-70 mM, about 20-80 mM, about 30-40 mM, about 30-50 mM, about 30-60 mM, about 30-70 mM, about 30-80 mM, about 40-50 mM, about 40-60 mM, about 40-70 mM, about 40-80 mM, about 50-60 mM, about 50-70 mM, about 50-80 mM, about 60-70 mM, about 60-80 mM, or about 70-80 mM. In other embodiments, the concentration of MES is about 40-45 mM, about 45-50 mM, about 50-55 mM, or about 55-60 mM.

In some embodiments, the concentration of MOPS is about 10 mM, about 20 mM, about 30 mM, about 40 mM, about 45 mM, about 50 mM, about 55 mM, about 60 mM, about 70 mM, about 80 mM, about 100 mM, or greater. In some embodiments, the concentration of MOPS is about 20-30 mM, about 20-40 mM, about 20-50 mM, about 20-60 mM, about 20-70 mM, about 20-80 mM, about 30-40 mM, about 30-50 mM, about 30-60 mM, about 30-70 mM, about 30-80 mM, about 40-50 mM, about 40-60 mM, about 40-70 mM, about 40-80 mM, about 50-60 mM, about 50-70 mM, about 50-80 mM, about 60-70 mM, about 60-80 mM, or about 70-80 mM. In other embodiments, the concentration of MOPSO is about 40-45 mM, about 45-50 mM, about 50-55 mM, or about 55-60 mM.

In some embodiments, the concentration of MOPSO is about 10 mM, about 20 mM, about 30 mM, about 40 mM, about 45 mM, about 50 mM, about 55 mM, about 60 mM, about 70 mM, about 80 mM, about 100 mM, or greater. In some embodiments, the concentration of MOPSO is about 20-30 mM, about 20-40 mM, about 20-50 mM, about 20-60 mM, about 20-70 mM, about 20-80 mM, about 30-40 mM, about 30-50 mM, about 30-60 mM, about 30-70 mM, about 30-80 mM, about 40-50 mM, about 40-60 mM, about 40-70 mM, about 40-80 mM, about 50-60 mM, about 50-70 mM, about 50-80 mM, about 60-70 mM, about 60-80 mM, or about 70-80 mM. In other embodiments, the concentration of MOPSO is about 40-45 mM, about 45-50 mM, about 50-55 mM, or about 55-60 mM.

In some embodiments, the concentration of ACES is about 10 mM, about 20 mM, about 30 mM, about 40 mM, about 45 mM, about 50 mM, about 55 mM, about 60 mM, about 70 mM, about 80 mM, about 100 mM, or greater. In some embodiments, the concentration of ACES is about 20-30 mM, about 20-40 mM, about 20-50 mM, about 20-60 mM, about 20-70 mM, about 20-80 mM, about 30-40 mM, about 30-50 mM, about 30-60 mM, about 30-70 mM, about 30-80 mM, about 40-50 mM, about 40-60 mM, about 40-70 mM, about 40-80 mM, about 50-60 mM, about 50-70 mM, about 50-80 mM, about 60-70 mM, about 60-80 mM, or about 70-80 mM. In other embodiments, the concentration of ACES is about 40-45 mM, about 45-50 mM, about 50-55 mM, or about 55-60 mM.

In some embodiments, the concentration of the basic buffer is about 5 mM, 10 mM, about 15 mM, about 20 mM, about 30 mM, about 40 mM, about 50 mM, about 60 mM, about 70 mM, about 80 mM, about 90 mM, about 100 mM, about 110 mM, about 120 mM, about 130 mM, about 140 mM, about, about 150 mM, about 160 mM, about 170 mM, about 180 mM, about 190 mM, about 200 mM, or greater. In certain embodiments, the concentration of the basic buffer is about 5-10 mM, about 5-15 mM, about 5-20 mM, about 5-25 mM, about 10-15 mM, about 10-20 mM, about 10-25 mM, about 15-20 mM, about 15-25 mM, or about 20-25 mM. In other embodiments, the concentration of the basic buffer is about 10-15 mM. In yet other embodiments, the concentration of the basic buffer is about 11.5-14.5 mM.

In some embodiments, the concentration of Arginine is about 10 mM, about 20 mM, about 30 mM, about 40 mM, about 50 mM, about 60 mM, about 70 mM, about 80 mM, about 90 mM, about 100 mM, about 110 mM, about 120 mM, about 130 mM, about 140 mM, about, about 150 mM, about 160 mM, about 170 mM, about 180 mM, about 190 mM, about 200 mM. In certain embodiments, the concentration of Arginine is about 5-10 mM, about 5-15 mM, about 5-20 mM, about 5-25 mM, about 10-15 mM, about 10-20 mM, about 10-25 mM, about 15-20 mM, about 15-25 mM, or about 20-25 mM. In other embodiments, the concentration of Arginine is about 10-15 mM. In yet other embodiments, the concentration of Arginine is about 11.5-14.5 mM. In yet other embodiments, the concentration of Arginine is about 18 mM.

In some embodiments, the concentration of BTP is about 10 mM, about 12.5 mM, about 15 mM, about 17.5 mM, about 20 mM, about 22 mM, about 25 mM, about 28 mM, about 30 mM, about 40 mM, about 50 mM, about 60 mM, about 70 mM, about 80 mM, about 100 mM, or greater. In certain embodiments, the concentration of BTP is about 5-10 mM, about 5-15 mM, about 5-20 mM, about 5-25 mM, about 10-15 mM, about 10-20 mM, about 10-25 mM, about 15-20 mM, about 15-25 mM, or about 20-25 mM. In other embodiments, the concentration of BTP is about 10-15 mM. In yet other embodiments, the concentration of BTP is about 11.5-14.5 mM. In other embodiments, the concentration of BTP is about 13-14 mM. In yet other embodiments, the concentration of BTP is about 10-11 mM, about 11-12 mM, about 12-13 mM, about 13-14 mM, about 14-15 mM, or about 15-16 mM. In some embodiments, concentration of BTP is about 10 mM. In some embodiments, concentration of BTP is about 10.5 mM. In some embodiments, concentration of BTP is about 11 mM. In some embodiments, concentration of BTP is about 11.5 mM. In some embodiments, concentration of BTP is about 12 mM.

In certain embodiments, the buffer pH is titrated with the basic buffer, e.g., such that the desired concentration of the acid buffer (e.g., one or more of MES, MOPS, MOPSO, ACES, and derivatives thereof) and desired pH determines the concentration of the basic buffer (e.g., one more more of Arginine and BTP). Advantageously, the low conductivity is maintained. Thus, advantageously, the desired pH is obtained by calculation of the ratio of acidic buffer to basic buffer, or by titration of basic buffer against acidic buffer, and not, as is common in the art, titration using strong acids and bases (e.g. sodium hydroxide or hydrogen chloride.) Thus, generally first the concentration of the acidic buffer and the desired pH are chosen and then the concentration of the basic buffer is determined by titration, or by the Henderson-Hasselbalch equation:

$$pH = pK_a + \log\left(\frac{[base]}{[acid]}\right).$$

Alternatively, the concentration of the basic buffer and the desired pH are chosen and then the concentration of the acid buffer is determined by titration, or by the Henderson-Hasselbalch equation.

As used herein, "EDTA" refers to ethylenediaminetetraacetic acid. ETDA is an aminopolycarboxylic acid. Its conjugate base is ethylenediaminetetraacetate. Without being bound by theory, advantageously EDTA acts as a chelating again via its hexadentate ligand-binding moieties. EDTA sequesters metal ions such as $Ca^{2+}$ and $Fe^{3+}$. After being bound by EDTA into a metal complex, metal ions remain in solution but exhibit diminished reactivity. EDTA is produced as several salts, notably disodium EDTA and calcium disodium EDTA. The chemical structure of EDTA is:

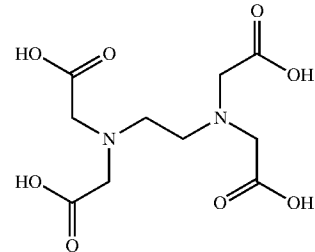 [SMILES: O=C(O)CN(CCN(CC(=O)O)CC(=O)O)CC(=O)O]

In some embodiments, the sample loading buffer comprises EDTA. In some embodiments, the concentration of EDTA is about 0.1 mM to about 0.5 mM or about 0.5 mM to 1.0 mM. In some embodiments, the concentration of EDTA is about 0.1 mM, about 0.2 mM, about 0.3 mM, about 0.4 mM, about 0.5 mM, 0.6 mM, about 0.7 mM, about 0.8 mM, about 0.9 mM, about 1.0 mM. In some embodiments, the concentration of EDTA is about 1.0 mM, 2.0 mM, or 3.0 mM.

In some embodiments, the sample loading buffer comprises a chelating agent other than EDTA used alone or in combination with EDTA.

As used herein, "IAM" refers to 2-Iodoacetamide. IAM is used in the art used to bind covalently with the thiol group of cysteine of a protein so that the protein cannot form disulfide bonds. The chemical structure of IAM is:

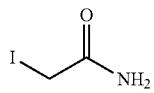

In some embodiments, the sample loading buffer comprises IAM. In some embodiments, the concentration of IAM is about 0.1 mM to about 0.5 mM or about 0.5 mM to 1.0 mM. In some embodiments, the concentration of EDTA is about 0.1 mM, about 0.2 mM, about 0.3 mM, about 0.4 mM, about 0.5 mM, 0.6 mM, about 0.7 mM, about 0.8 mM, about 0.9 mM, about 1.0 mM. In some embodiments, the concentration of IAM is about 1.0 mM, 2.0 mM, or 3.0 mM.

In some embodiments, the sample loading buffer comprises a alkylating agent other than IAM used alone or in combination with IAM.

In some embodiments, the sample loading buffer comprises SDS. In some embodiments, the concentration of SDS is about 0.1% v/v to about 0.5% v/v or about 0.5% v/v to 1.0% v/v. In some embodiments, the concentration of SDS is about 0.1% v/v, about 0.2% v/v, about 0.3% v/v, about 0.4% v/v, about 0.5% v/v, 0.6% v/v, about 0.7% v/v, about 0.8% v/v, about 0.9% v/v, about 1.0% v/v. In some embodiments, the concentration of SDS is about 0.1% w/v to about 0.5% w/v or about 0.5% w/v to 1.0% w/v. In some embodiments, the concentration of SDS is about 0.1% w/v, about 0.2% w/v, about 0.3% w/v, about 0.4% w/v, about 0.5% w/v, 0.6% w/v, about 0.7% w/v, about 0.8% w/v, about 0.9% w/v, about 1.0% w/v.

In some embodiments, the sample loading buffer comprises glycerol. In some embodiments, the concentration of glycerol is about 0.1% v/v to about 0.5% v/v or about 0.5% v/v to 1.0% v/v. In some embodiments, the concentration of glycerol is about 0.1% v/v, about 0.2% v/v, about 0.3% v/v, about 0.4% v/v, about 0.5% v/v, 0.6% v/v, about 0.7% v/v, about 0.8% v/v, about 0.9% v/v, about 1.0% v/v. In some embodiments, the concentration of glycerol is about 0.1% w/v to about 0.5% w/v or about 0.5% w/v to 1.0% w/v. In some embodiments, the concentration of glycerol is about 0.1% w/v, about 0.2% w/v, about 0.3% w/v, about 0.4% w/v, about 0.5% w/v, 0.6% w/v, about 0.7% w/v, about 0.8% w/v, about 0.9% w/v, about 1.0% w/v. Alternative to glycerol include other polyols, including but not limited to sorbitol, mannitol, maltitol, lactitol, xylitol, isomalt, and erythritol.

In some embodiments, the sample loading buffer comprises sucrose. In some embodiments, the concentration of sucrose is about 0.1% v/v to about 0.5% v/v or about 0.5% v/v to 1.0% v/v. In some embodiments, the concentration of sucrose is about 0.1% v/v, about 0.2% v/v, about 0.3% v/v, about 0.4% v/v, about 0.5% v/v, 0.6% v/v, about 0.7% v/v, about 0.8% v/v, about 0.9% v/v, about 1.0% v/v. In some embodiments, the concentration of sucrose is about 0.1% w/v to about 0.5% w/v or about 0.5% w/v to 1.0% w/v. In some embodiments, the concentration of sucrose is about 0.1% w/v, about 0.2% w/v, about 0.3% w/v, about 0.4% w/v, about 0.5% w/v, 0.6% w/v, about 0.7% w/v, about 0.8% w/v, about 0.9% w/v, about 1.0% w/v. Alternative to sucrose include other sugars.

In some embodiments, the sample loading buffer comprises a reducing agent. In some embodiments, the reducing agent comprises dithiothreitol (DTT). In some embodiments, the reducing agent comprises β-mercaptoethanol (BME). Other reducing agents may be used. In some embodiments, the concentration of DTT is about 0.1 mM to about 0.5 mM or about 0.5 mM to 1.0 mM. In some embodiments, the concentration of DTT is about 0.1 mM, about 0.2 mM, about 0.3 mM, about 0.4 mM, about 0.5 mM, 0.6 mM, about 0.7 mM, about 0.8 mM, about 0.9 mM, about 1.0 mM. In some embodiments, the concentration of BME is about 1.0 mM, 2.0 mM, or 3.0 mM. In some embodiments, the concentration of BME is about 0.1 mM to about 0.5 mM or about 0.5 mM to 1.0 mM. In some embodiments, the concentration of BME is about 0.1 mM, about 0.2 mM, about 0.3 mM, about 0.4 mM, about 0.5 mM, 0.6 mM, about 0.7 mM, about 0.8 mM, about 0.9 mM, about 1.0 mM. In some embodiments, the concentration of BME is about 1.0 mM, 2.0 mM, or 3.0 mM.

In some embodiments, the concentrations of chelating agent, glycerol/polyol, and/or reducing agent is compatible with CE-SDS. In some embodiments, the sample loading buffer is suitable for, adapted for, or compatible with capillary electrophoresis with sodium dodecylsuflate (CE-SDS). In some embodiments, the sample loading buffer is suitable for, adapted for, or compatible with capillary electrophoresis with electrokinetic injection. In some embodiments, the sample loading buffer is suitable for, adapted for, or compatible with capillary electrophoresis with electrokinetic injection. In some embodiments, the sample loading buffer is suitable for, adapted for, or compatible with capillary electrophoresis with pressure injection.

In some embodiments, CE-SDS performed using the sample loading buffer has sensitivity at least 10%, at least 20%, at least 30%, at least 40%, at least 50%, at least 60%, at least 70%, at least 80%, at least 90%, or at least 95% as great as the sensitivity of CE-SDS using 100 mM Tris-HCl, 1.0% SDS, pH 9.0 as the sample loading buffer. In some embodiments, CE-SDS performed using the sample loading buffer has sensitivity at least 10%, at least 20%, at least 30%, at least 40%, at least 50%, at least 60%, at least 70%, at least 80%, at least 90%, or at least 95% greater than the sensitivity of CE-SDS using 100 mM Tris-HCl, 1.0% SDS, pH 9.0 as the sample loading buffer.

In some embodiments, fragmentation of a polypeptide analyte is reduced compared to fragmentation of the same analyte in 100 mM Tris-HCl, 1.0% SDS, pH 9.0 as the sample loading buffer. In some embodiments, fragmentation of a polypeptide analyte is reduced at least 10%, at least 20%, at least 30%, at least 40%, at least 50%, at least 60%, at least 70%, at least 80%, at least 90%, or at least 95% compared to fragmentation of the same analyte in 100 mM Tris-HCl, 1.0% SDS, pH 9.0 as the sample loading buffer. In some embodiments, fragmentation of a polypeptide analyte is below detectible levels. In some embodiments, fragmentation is measured by CE-SDS. In some embodiments, fragmentation of a polypeptide analyte is reduced compared to fragmentation of the same analyte in 100 mM Tris-HCl, 1.0% SDS, pH 9.0 as the sample loading buffer. In some embodiments, the polypeptide analyte is rituximab, bevacizumab, golimumab, cetuximab, entarecept, adalimumab, trastuzumab, or infliximab.

In another aspect, the disclosure provides methods for capillary electrophoresis, such as, but not limited to, CE-SDS. In some embodiments, the capillary electrophoresis comprises Capillary Zone Electrophoresis (CZE), Capillary Gel Electrophoresis (CGE), Capillary Isoelectric Focusing (cIEF), and Capillary Isotachophoresis (cITP). In some embodiments, the methods of the disclosure comprises performing polyacrylamide gel electrophoresis (PAGE), such as, but not limited to, SDS-PAGE.

In some embodiments, the method comprises providing an analyte comprising one or more polypeptides or a solution comprising said analyte. In some embodiments, the method comprises contacting the analyte or solution with a sample loading buffer, thereby generating a sample. In some embodiments, the method comprises loading the sample onto a capillary. In some embodiments, the method comprises applying a voltage across the capillary to resolve the one or more polypeptides. In some embodiments, the method comprises detecting the one or more polypeptides.

In some embodiments, the loading step of the method comprises electrokinetic injection. In some embodiments, the loading step comprises applying a voltage of at least about 1,000 V, at least about 2,000 V, at least about 3,000 V, at least about 4,000 V, at least about 4,600 V, at least about 5,000 V, at least about 6,000 V, at least about 7,000 V, or greater across the capillary.

In some embodiments, the voltage used for electrokinetic injection is applied for about 10 to about 30 seconds. In some embodiments, the voltage used for electrokinetic injection is applied for about 10, about, 20, about 30, about 40, about 50, or to about 60 seconds.

In another aspect, the disclosure a kit for CE-SDS, comprising the sample loading buffer of the disclosure and, optionally a capillary. The kit may also comprises one or more of instructions for use, a container for the sample loading buffer, a reference analyte, and a standard or set of standards.

In some embodiments, electrophoresis is performed in buffers which exhibit both substantial buffering capacity and low electrical conductivity. Advantageously, this permits the separations to be performed at high field strengths without loss of resolution. Advantageously, this increases the sensitivity. Without being bound by theory, the loading efficiency via electrokinetic sample injection is higher when electric conductivity is lower. Advantageously, high injection efficiency is maintained despite a decrease in pH compared to other sample loading buffers.

The disclosure further provides the following numbered embodiments:

1. A method for capillary electrophoresis, comprising:
   a) providing an analyte comprising one or more polypeptides or a solution comprising said analyte,
   b) contacting the analyte or solution of step (a) with a sample loading buffer, thereby generating a sample,
   c) loading the sample onto a capillary,
   d) applying a voltage across the capillary to resolve the one or more polypeptides,
   e) detecting the one or more polypeptides,
   wherein the sample loading buffer is a buffered aqueous solution comprising an acidic buffer selected from MES, MOPS, MOPSO, and ACES and a basic buffer selected from Arginine and BTP.
2. The method of embodiment 1, wherein the sample loading buffer has a pH of about 6.0 to about 7.6.
3. The method of embodiment 1 or embodiment 2, wherein the sample loading buffer has a pH of about 7.0 to about 7.4.
4. The method of any one of embodiments 1 to 3, wherein the sample loading buffer has a conductivity of 2.0 mS/cm or less.
5. The method of any one of embodiments 1 to 4, wherein the concentration of acidic buffer in the sample loading buffer is about 50 mM.
6. The method of any one of embodiments 1 to 5, wherein the sample loading buffer comprises one or more of EDTA, SDS, and glycerol at concentrations compatible with CE-SDS.
7. The method of any one of embodiments 1 to 6, wherein the loading step (c) comprises electrokinetic injection
8. The method of embodiment 7, wherein the loading step (c) comprises applying a voltage of about 5,000 V across the capillary for about 10 to about 30 seconds.
9. The method of any one of embodiments 1 to 8, wherein the sensitivity of the method is at least 90% as great as the sensitivity of the method performed using 100 mM Tris-HCl, 1.0% SDS, pH 9.0 as the sample loading buffer.
10. The method of any one of embodiments 1 to 9, wherein fragmentation of at least one of the polypeptides in the analyte is reduced compared to the fragmentation of the same analyte when the method is performed using 100 mM Tris-HCl, 1.0% SDS, pH 9.0 as the sample loading buffer.
11. The method of embodiment 9 or embodiment 10, wherein the analyte comprises rituximab, bevacizumab, golimumab, cetuximab, entarecept, adalimumab, trastuzumab, or infliximab.
12. The method of any one of embodiments 1 to 11, wherein the method comprises Capillary Zone Electrophoresis (CZE), Capillary Gel Electrophoresis (CGE), Capillary Isoelectric Focusing (cIEF), and Capillary Isotachophoresis (cITP)
13. A sample loading buffer, comprising a buffered aqueous solution comprising an acidic buffer selected from MES, MOPS, MOPSO, and ACES and a basic buffer selected from Arginine and BTP, wherein the sample loading buffer has a pH of about 6.0 to about 7.6.
14. The sample loading buffer of embodiment 13, wherein the sample loading buffer has a pH of about 7.0 to about 7.4.
15. The sample loading buffer of embodiment 13 or embodiment 14, wherein the sample loading buffer has a conductivity of 2.0 mS/cm or less.
16. The sample loading buffer of any one of embodiments 13 to 15, wherein the concentration of acidic buffer in the sample loading buffer is about 50 mM.
17. The sample loading buffer of any one of embodiments 13 to 16, wherein the sample loading buffer comprises one or more of EDTA, SDS, and glycerol at concentrations compatible with CE-SDS.
18. The sample loading buffer of any one of embodiments 13 to 17, wherein the sample loading buffer is suitable for capillary electrophoresis with sodium dodecylsulfate (CE-SDS).
19. The sample loading buffer of any one of embodiments 13 to 18, wherein CE-SDS performed using the sample loading buffer has sensitivity at least 90% as great as the sensitivity of CE-SDS using 100 mM Tris-HCl, 1.0% SDS, pH 9.0 as the sample loading buffer.
20. The sample loading buffer of any one of embodiments 13 to 19, wherein fragmentation of a polypeptide analyte measured by CE-SDS is reduced compared to fragmentation of the same analyte in 100 mM Tris-HCl, 1.0% SDS, pH 9.0 as the sample loading buffer.
21. The method of embodiment 19 or embodiment 20, wherein the analyte comprises rituximab, bevacizumab, golimumab, cetuximab, entarecept, adalimumab, trastuzumab, or infliximab.
22. A kit for CE-SDS, comprising the sample loading buffer of any one of embodiments 13 to 21 and a capillary suitable for CE-SDS.

EXAMPLES

Generally the Examples described below employed the following materials, samples, and methods. Standard methods for the ProteinSimple® Maurice™ Biosimilar Platform CE-SDS were employed.

Materials
ProteinSimple® Maurice™ CE-SDS cartridge
ProteinSimple® Maurice™ CE-SDS Size Application Kit Samples
Therapeutic antibody from innovators and biosimilars.
R&D Systems® recombinant mAb Analytical Standards, including rituximab, bevacizumab, trastuzumab, adalimumab and cetuximab.
Antibodies: Rituximab-Recombinant Monoclonal Human IgG1 Clone #Hu2. Catalog Number: MAB9575. Trastuzumab-Recombinant Monoclonal Human IgG1 Clone #Hu5. Catalog Number: MAB9589. Adalimumab-Recombinant Monoclonal Human IgG Clone #Hu7. Catalog Number: MAB9677. Cetuximab-Recombinant Monoclonal Human IgG Clone #Hu1. Catalog Number: MAB9577.

Methods
Samples were diluted to 1.0 mg/mL (1.5 mg/mL for cetuximab and entarecept) with 1X Maurice Sample Buffer and supplemented with the 10 kDa internal standard (IS) prior to treatment for 10 minutes at 70° C. in the presence of 11.5 mM iodoacetamide (IAM).

Samples were injected into the capillary for 20 seconds at 4,600 V, and then separation was performed by applying at 5,750 V across the capillary for 35 minutes. Size variants were detected by absorbance at 220 nm and analyzed with Compass for iCE software.

Example 1: Standard CE-SDS Sample Buffers can Thermally Induce Fragmentation During Heating It has been observed that under slightly acidic conditions (pH 5.5-6.5) the thermally induced fragmentation of non-reduced at least one monoclonal antibody is greatly decreased. Zhang et al. *J Pharm Biomed Anal.* 2010 Dec. 15; 53(5): 1236-43. As fragmentation of proteins, particularly antibodies, is known to be correlated with pH, because the hinge region of the immunoglobulin is base-liable. Thus, lower solution pH decreases fragmentation. Nevertheless, lowering sample loading buffer pH, by itself, is not an ideal solution to the problem fragmentation, because low pH sample loading buffers typically result in poor performance (FIGS. 1A-1E). This means that the industry has an unmet need for improved sample loading buffers, particularly for antibody or more generally biologic drugs.

Experiments to assess separation characteristics were performed and reported in Table 1.

TABLE 1

Exemplary CE-SDS Results

| Sample Buffer | Peak Area | Peak Area (%) | Impurity Peak Area | Impurity Peak Area (%) |
|---|---|---|---|---|
| High-performance liquid chromatography size exclusion chromatograph HPLC-SEC | | | | |
| | 16,474 | 98.5 | 140 | 0.8 |
| CE-SDS | | | | |
| 100 mM Tris-HCl, 1.0% SDS, pH 9.0 | 51,972 | 96.4 | 1227 | 2.3 |
| 100 mM Tris-HCl, 1.0% SDS, pH 7.5 | 17,283 | 98.3 | 224 | 1.3 |
| 50 mM citrate-phosphate, 1.0% SDS, pH 6.75 | 26,126 | 98.2 | 319 | 1.2 |
| 75 mM citrate-phosphate, 1.0% SDS, pH 6.75 | 12,702 | 98.4 | 152 | 1.2 |

In further experiments, citrate-phosphate and morpholinoethanesulfonic acid/morpholinoethanesulfonate (MES/MES base) buffer-system sample loading buffers exhibited reduced sensitivity and changes the internal standard (IS) peak shape compared to other buffers. As such, a citrate-phosphate buffer at pH 6.5 was used for sample preparation to replace the original Beckman sample buffer (pH 9.0). The optimal sample preparation conditions were found to be as follows: (1) incubation temperature and duration (reduced and non-reduced), 65 degrees C. for 5 min; (2) alkylation condition, 10 µL of 0.25 M IAM; (3) reduction condition, 10 micro L of 5-fold diluted 2-ME.

The method was qualified by evaluating specificity, accuracy, precision, limit of quantitation (LOQ), and linearity. The method exhibited no interference from sample buffer matrix. The method was found to be linear, accurate, and precise in the range of 0.25-3.0 mg/mL protein concentration. The LOQ of the method was determined to be 0.02 mg/mL for reduced and non-reduced mAb1. In addition, some aspects of sample stability were examined during qualification.

Example 2: Development of Alternative Buffer Systems

Sample buffer candidates were developed and tested for high injection efficiency and low fragmentation. First, physical properties of various buffer systems were examined. Conductivity of solutions is reported in TABLE 2.

TABLE 2

Exemplary Buffer Systems

| Buffer | pH | Conductivity (mS/cm) | Peak Height |
|---|---|---|---|
| MOPS-Arg | 6.53 | 1.5 | High |
| MOPS-BTP | 6.49 | 1.6 | High |
| MOPSO-BTP | 6.48 | 1.8 | High |
| ACES-BTP | 6.52 | 1.9 | High |
| ProteinSimple ® Sample Buffer (SB) Maurice CE-SDS 1X Sample Buffer | 9.50 | 2.0 | High |
| Beckman ® SB | 9.00 | 2.3 | High |
| MES-Arg | 6.50 | 2.4 | High |
| MES-Tris | 6.51 | 2.5 | High |
| Citric acid-Arg | 6.61 | 6.7 | Low |
| Citric acid-Phosphate | 6.50 | 8.6 | Low |
| MES-MES Base | 6.52 | 9.7 | Low |

Buffer systems were adapted for CE-SDS by addition of SDS at 1% v/v using the volumes detailed in Table 3. The MOPS solution was prepared by dissolving 0.451 g MOPS in 20 mL water. The BTP solution was prepared by dissolving 0.418 g BTP in 20 mL water. The Arg solution was prepared by dissolving 0.871 g L-arginine in 10 mL water. As indicated EDTA at 1 mM or glycerol at 5% v/v were added. SDS was provided at 20% v/v. Solutions of the indicated acid, the indicated base, SDS, and optionally EDTA or glycerol were added to water, mixed, and then more water was added to reach a total volume of 40 mL [Quantum satis (QS), i.e. as much as sufficient to reach total volume].

TABLE 3

Preparation of Exemplary CE-SDS Sample Loading Buffers

| | MOPS (mL) | Arg (mL) | BTP (mL) | SDS (mL) | Water |
|---|---|---|---|---|---|
| 50 mM MOPS-Arg pH 6.5; 1% SDS | 20 | 5.5 | | 2 | To 40 mL |
| 50 mM MOPS-Arg pH 6.5; 1% SDS | 20 | 5.5 | | [EDTA] | To 40 mL |
| 50 mM MOPS-Arg pH 6.5; 1 mM EDTA; 5% Glycerol; 1% SDS | 20 | 5.5 | | [glycerol] | To 40 mL |
| 50 mM MOPS-BTP pH. 6.5; 1% SDS | 20 | | 14 | 2 | To 40 mL |

Further buffer systems were made as detailed in Table 4. The MOPS solution was prepared by dissolving 0.451 g MOPS in 20 mL water. The BTP solution was prepared by dissolving 0.418 g BTP in 20 mL water. The Arg solution was prepared by dissolving 0.871 g L-arginine in 10 mL water. As indicated EDTA at 1 mM or glycerol at 5% v/v were added. SDS was provided at 20% v/v. Solutions of the indicated acid, the indicated base, SDS, and optionally EDTA or glycerol were added to water, mixed, and then more water was added to reach a total volume of 40 mL [Quantum satis (QS), i.e. as much as sufficient to reach total volume].

TABLE 4

Preparation of Exemplary CE-SDS Sample Loading Buffers

| | MOPS (g) | MES (g) | MES base (g) | Arg (g) | Citrate (g) | SDS (mL) | Water |
|---|---|---|---|---|---|---|---|
| 150 mM Citrate-Arg pH 6.5; 1% SDS | | | | 0.871 | 0.312 | 2 | To 40 mL |
| 250 mM MES pH 6.5; 1% SDS | | 0.780 | 1.610 | | | [EDTA] | To 40 mL |
| 350 mM MOPS-Arg pH 6.5; 1% SDS | 0.312 | | | 0.871 | | [glycerol] | To 40 mL |
| 450 mM MOPS-Arg pH. 6.5 | 0.451 | | | 0.871 | | 2 | To 40 mL |

Several candidates showed high efficiency and low fragmentation but altered peak shapes or selectivity (FIG. 2 and FIGS. 3A-4B). Generally lower conductivity improved separation performance under CE-SDS. A final candidate obtained the required high efficiency and low fragmentation with the expected peak profiles.

Figure 4A:
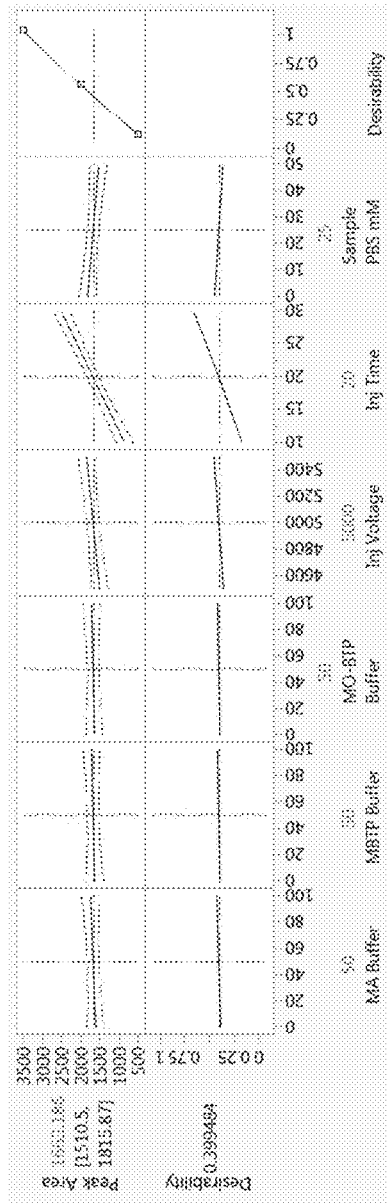
FIGS. 4A-4C show results for Design of Experiments (DOE) experiment. Peak Area (FIG. 4A) and Peak Area Loss (FIG. 4B) were measured and favorability was calculated (FIG. 4C). MA, MOPS-Arg; MBTP, MOPS-BTP; MO-BTP, MOPSO-BTP; Inj Voltage, injection voltage; Inj time, injection time; PBS, phosphate buffered saline.
Figure 4B:
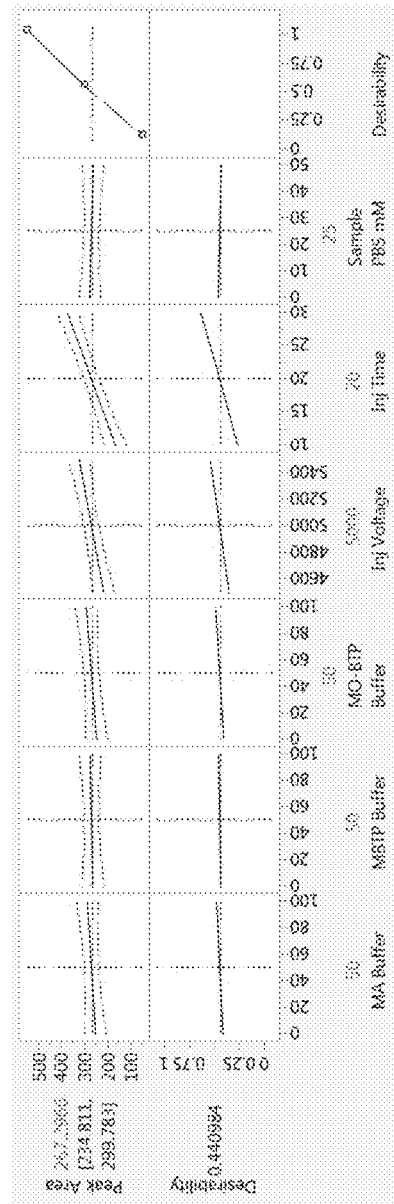
Figure 4C:
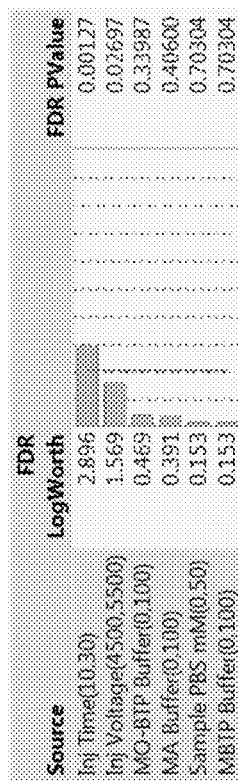

A Design of Experiments (DOE) experiment demonstrated that the tested buffers were robust to variation in concentration, injection voltage, injection time, and concentration of phosphate-buffered saline (PBS) in the sample prior to mixing the sample with the sample loading buffer (Table 4 and FIGS. 4A-4C).

TABLE 4

DOE Experimental Design

| | Pattern | MOPS-Arg Buffer (mM) | MOPS-BTP Buffer (mM) | MOPSO-BTP Buffer(mM) | Sample PBS (mM) | Inj Voltage | Inj Time |
|---|---|---|---|---|---|---|---|
| 1 | +−+++− | 100 | 0 | 100 | 0 | 5500 | 30 |
| 2 | −+++−− | 0 | 100 | 100 | 0 | 5500 | 10 |
| 3 | 0 | 50 | 50 | 50 | 25 | 5000 | 20 |
| 4 | +−−+−+ | 100 | 0 | 0 | 50 | 5500 | 10 |
| 5 | 0 | 50 | 50 | 50 | 25 | 5000 | 20 |
| 6 | +++−−− | 100 | 100 | 100 | 0 | 4500 | 10 |
| 7 | −+−+++ | 0 | 100 | 0 | 50 | 5500 | 30 |
| 8 | −−+−−+ | 0 | 0 | 100 | 50 | 4500 | 10 |
| 9 | ++++++ | 100 | 100 | 100 | 50 | 5500 | 30 |
| 10 | +−−−+− | 100 | 0 | 0 | 0 | 4500 | 30 |
| 11 | −−+−++ | 0 | 0 | 100 | 50 | 4500 | 30 |
| 12 | ++−−−+ | 100 | 100 | 0 | 50 | 4500 | 10 |
| 13 | −+−+−− | 0 | 100 | 0 | 0 | 4500 | 30 |
| 14 | −−−−+− | 0 | 0 | 0 | 0 | 5500 | 10 |

Example 3: Testing of Final Buffer Candidate

Extensive testing and optimization were performed to arrive at a final buffer candidate. Exemplary testing results are provide in the tables below. Results with trastuzumab (Her2), rituximab (RIT), bevacizumab (AVI), and golimumab (SIM) are shown in Table 5 and Table 6. Experiments were before under non-reducing conditions but with IAM, in duplicate series.

TABLE 5

| Buffer | Abbreviation |
|---|---|
| 50 mM MOPS-Bis Tris Propane pH 6.5 | M-BTP |
| 50 mM MOPSO-Arg pH 6.5 | MO-Arg |
| 50 mM MOPSO-Bis Tris Propane pH 6.5 | MO-BTP |

TABLE 6

| Sample | Concentration (mg/mL) | Treatment | Injection |
|---|---|---|---|
| Her2 Inv | 0.75 | 70C_5m, No IAM | 15 sec 5500 V |
| Her2 Rec | 0.75 | 70C_5m, No IAM | 15 sec 5500 V |
| RIT-ROC | 0.75 | 70C_5m, No IAM | 15 sec 5500 V |
| AVI-ZYD | 0.75 | 70C_5m, No IAM | 15 sec 5500 V |
| SIM-GOL | 0.75 | 70C_5m, No IAM | 15 sec 5500 V |

Further testing of biologic drugs was performed in MES/MES buffer systems, as shown in Tables 7A-7B and Tables 8A-8C.

TABLE 7A

| Non-Reduced | Sample | Percent Peak Area | | | | | | | | |
|---|---|---|---|---|---|---|---|---|---|---|
| | | LC | HC | HL | HH | HHL | NG | Intact | HMWS | MP Loss |
| Ps Sample Buffer | Her2_Inv_Std | 0.4 | 0.0 | 0.1 | 0.3 | 2.3 | 0.0 | 96.9 | 0.0 | N/A |
| 100 mM MES pH 6.5 | Her2_Inv_Mes | 0.1 | 0.0 | 0.2 | 0.2 | 1.0 | 0.0 | 98.5 | 0.0 | 1.6 |
| Ps Sample Buffer | Her2_Rec_Std | 1.8 | 0.3 | 0.6 | 1.5 | 6.3 | 1.2 | 88.4 | 0.0 | N/A |
| 100 mM MES pH 6.5 | Her2_Rec_Mes | 0.4 | 0.3 | 0.5 | 0.7 | 2.0 | 1.3 | 94.7 | 0.0 | 6.3 |
| Ps Sample Buffer | TRB-ROC_Std | 0.6 | 0.0 | 0.2 | 0.3 | 2.8 | 0.0 | 95.9 | 0.1 | N/A |
| 100 mM MES pH 6.5 | TRB-ROC_Mes | 0.1 | 0.0 | 0.2 | 0.1 | 1.0 | 0.0 | 98.6 | 0.0 | 2.7 |
| Ps Sample Buffer | CAN-Bio_Her2_Std | 0.6 | 0.1 | 0.1 | 0.3 | 3.2 | 0.0 | 95.7 | 0.2 | N/A |
| 100 mM MES pH 6.5 | CAN-Bio_Her2_Mes | 0.2 | 0.0 | 0.2 | 0.2 | 1.7 | 0.0 | 97.4 | 0.3 | 1.7 |

TABLE 7B

| Non-Reduced | Sample | Percent Peak Area | | | | | | | | |
|---|---|---|---|---|---|---|---|---|---|---|
| | | LC | HC | IHL | HH | HHL | NG | Intact | HMWS | MP Loss |
| Ps Sample Buffer | Rit_Inv_Std | 1.3 | 0.0 | 0.3 | 0.3 | 4.4 | 0.0 | 93.6 | 0.0 | N/A |
| 100 mM MES pH 6.5 | Rit_Inv_Mes | 0.7 | 0.1 | 0.4 | 0.1 | 2.1 | 0.0 | 96.7 | 0.0 | 3.1 |
| Ps Sample Buffer | Rit_Rec_Std | 1.9 | 0.5 | 0.4 | 1.3 | 5.3 | 6.0 | 84.6 | 0.0 | N/A |
| 100 mM MES pH 6.5 | Rit_Rec_Mes | 0.7 | 0.5 | 0.5 | 0.8 | 1.5 | 5.2 | 90.8 | 0.0 | 6.2 |
| Ps Sample Buffer | RIT-ROC_Std | 1.1 | 0.1 | 0.5 | 0.6 | 4.0 | 0.0 | 93.8 | 0.0 | N/A |
| 100 mM MES pH 6.5 | RIT-ROC_Mes | 0.5 | 0.1 | 0.6 | 0.2 | 1.7 | 0.0 | 97.0 | 0.0 | 3.2 |
| Ps Sample Buffer | RIT-Het_Std | 1.9 | 0.1 | 0.5 | 1.0 | 6.2 | 0.0 | 90.2 | 0.0 | N/A |
| 100 mM MES pH 6.5 | RIT-Het_Mes | 0.5 | 0.1 | 0.4 | 0.1 | 1.5 | 0.0 | 97.3 | 0.0 | 7.1 |

TABLE 7C

| Non-Reduced | Sample | Percent Peak Area | | | | | | | | |
|---|---|---|---|---|---|---|---|---|---|---|
| | | LC | HC | HL | HH | HHL | NG | Intact | HMWS | MP Loss |
| Ps Sample Buffer | Cet_Inv_Std | 0.9 | 0.0 | 0.1 | 0.0 | 1.2 | 0.0 | 97.8 | 0.0 | N/A |
| 100 mM MES pH 6.5 | Cet_Inv_Mes | 0.2 | 0.0 | 0.0 | 0.0 | 0.6 | 0.0 | 99.2 | 0.0 | 1.4 |
| Ps Sample Buffer | Cet_Rec_Std | 1.4 | 0.2 | 0.2 | 0.9 | 6.0 | 0.0 | 91.3 | 0.0 | N/A |
| 100 mM MES pH 6.5 | Cet_Rec_Mes | 0.3 | 0.2 | 0.6 | 0.4 | 2.3 | 0.0 | 96.2 | 0.0 | 4.9 |

TABLE 8A

| Non-Reduced | Sample | Percent Peak Area | | | | | | | | |
|---|---|---|---|---|---|---|---|---|---|---|
| | | LC | HC | HL | HH | HHL | NG | Intact | HMWS | MP Loss |
| Ps Sample Buffer | Ada_Inv_Std | 0.7 | 0.1 | 0.1 | 0.4 | 2.4 | 0.0 | 96.4 | 0.0 | N/A |
| 100 mM MES pH 6.5 | Ada_Inv_Mes | 0.2 | 0.0 | 0.2 | 0.2 | 1.1 | 0.0 | 98.3 | 0.0 | 1.9 |
| Ps Sample Buffer | Ada_Rec_Std | 1.9 | 0.7 | 0.5 | 1.4 | 5.9 | 0.0 | 88.3 | 1.3 | N/A |
| 100 mM MES pH 6.5 | Ada_Rec_Mes | 0.2 | 0.7 | 0.6 | 0.7 | 1.2 | 0.0 | 94.9 | 1.7 | 6.6 |
| Ps Sample Buffer | AVI-ZYD_Std | 0.8 | 0.1 | 0.3 | 0.6 | 3.7 | 0.0 | 94.5 | 0.0 | N/A |
| 100 mM MES pH 6.5 | AVI-ZYD_Mes | 0.4 | 0.1 | 0.3 | 0.5 | 2.3 | 0.0 | 96.4 | 0.0 | 1.9 |

TABLE 8B

| | | Percent Peak Area | | | | | | | | |
|---|---|---|---|---|---|---|---|---|---|---|
| Non-Reduced | Sample | LC | HC | HL | HH | HHL | NG | Intact | HMWS | MP Loss |
| Ps Sample Buffer | REM-INF_Std | 0.6 | 0.1 | 0.0 | 0.5 | 2.5 | 0.0 | 96.3 | 0.0 | N/A |
| 100 mM MES pH 6.5 | REM-INF_Mes | 0.1 | 0.0 | 0.0 | 0.3 | 0.8 | 0.0 | 98.7 | 0.0 | 2.4 |

TABLE 8C

| Non-Reduced | Sample | Percent Peak Area | | | | | | | | |
|---|---|---|---|---|---|---|---|---|---|---|
| | | LC | HC | HL | HH | HHL | NG | Intact | HMWS | MP Loss |
| Ps Sample Buffer | SIM-GOL_Std | 0.6 | 0.1 | 0.2 | 0.5 | 2.6 | 0.0 | 96.0 | 0.0 | N/A |
| 100 mM MES pH 6.5 | SIM-GOL_Mes | 0.2 | 0.1 | 0.3 | 0.3 | 0.8 | 0.0 | 98.3 | 0.0 | 2.3 |

A final sample buffer candidate was selected from within the concentration and pH ranges that follow: MOPS-BTP, pH range: 6.0-7.6, or more precisely pH range: 7.0-7.4; 40-60 mM MOPS and, depending on the pH selected, which was used to the concentration of the basic buffer, 10-15 mM BTP, or more precisely 11.5-14.5 mM BTP, or even more precisely, 13-14 mM BTP.

Figure 5A:
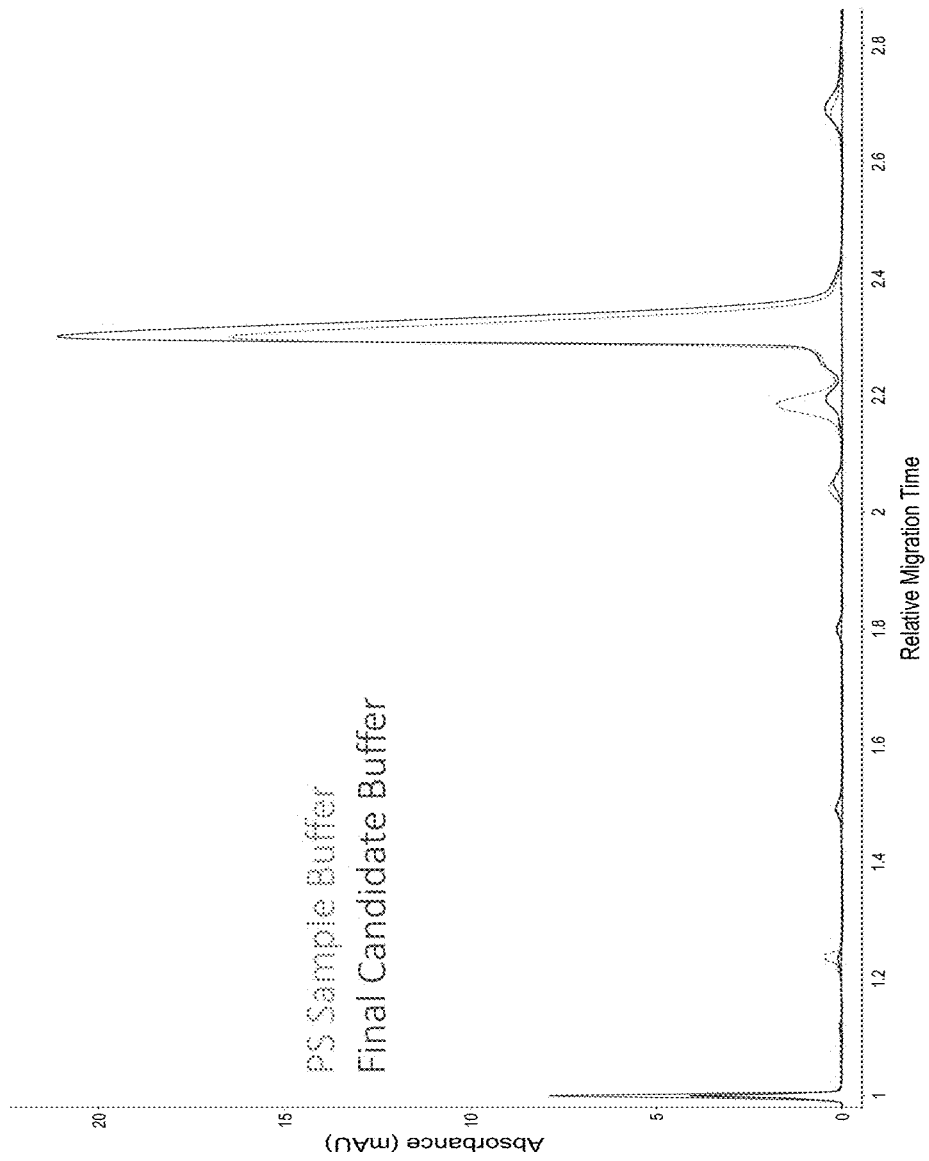
FIGS. 5A-5B shows that final sample buffer candidate shows superior performance.
Figure 5B:
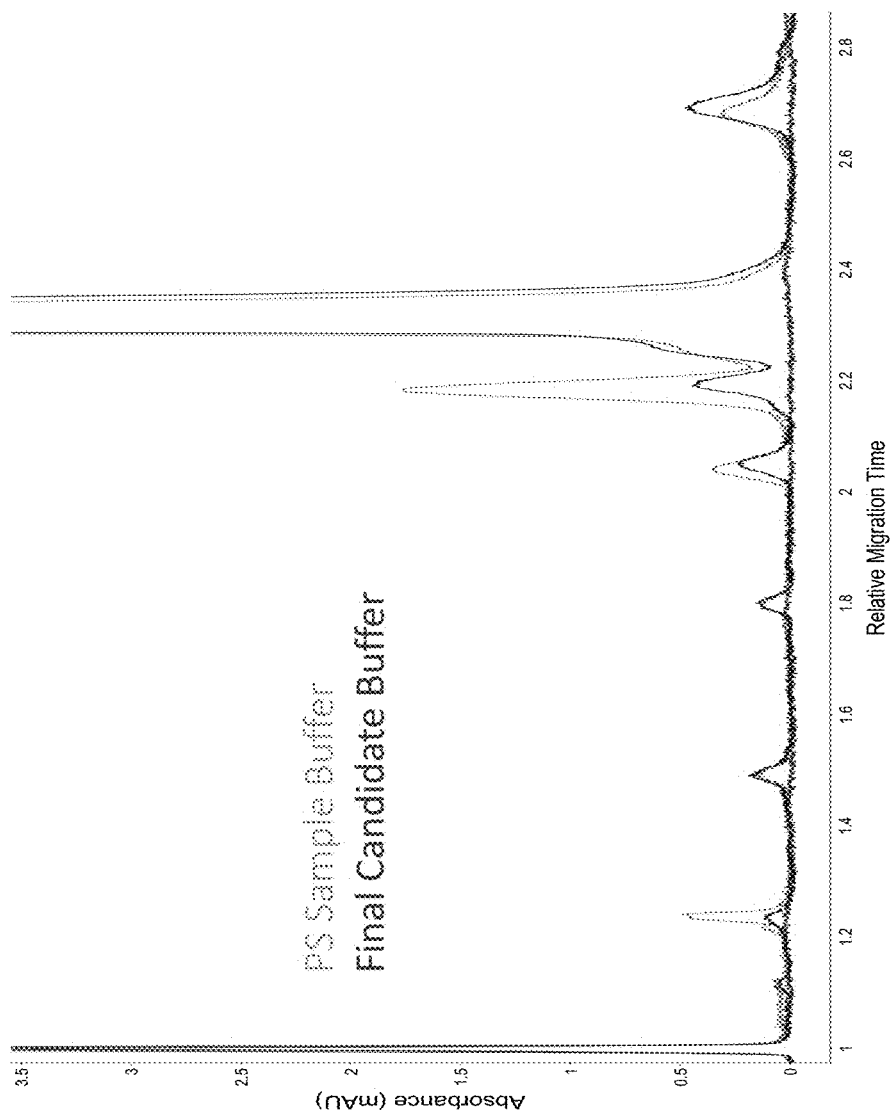
Figure 6:
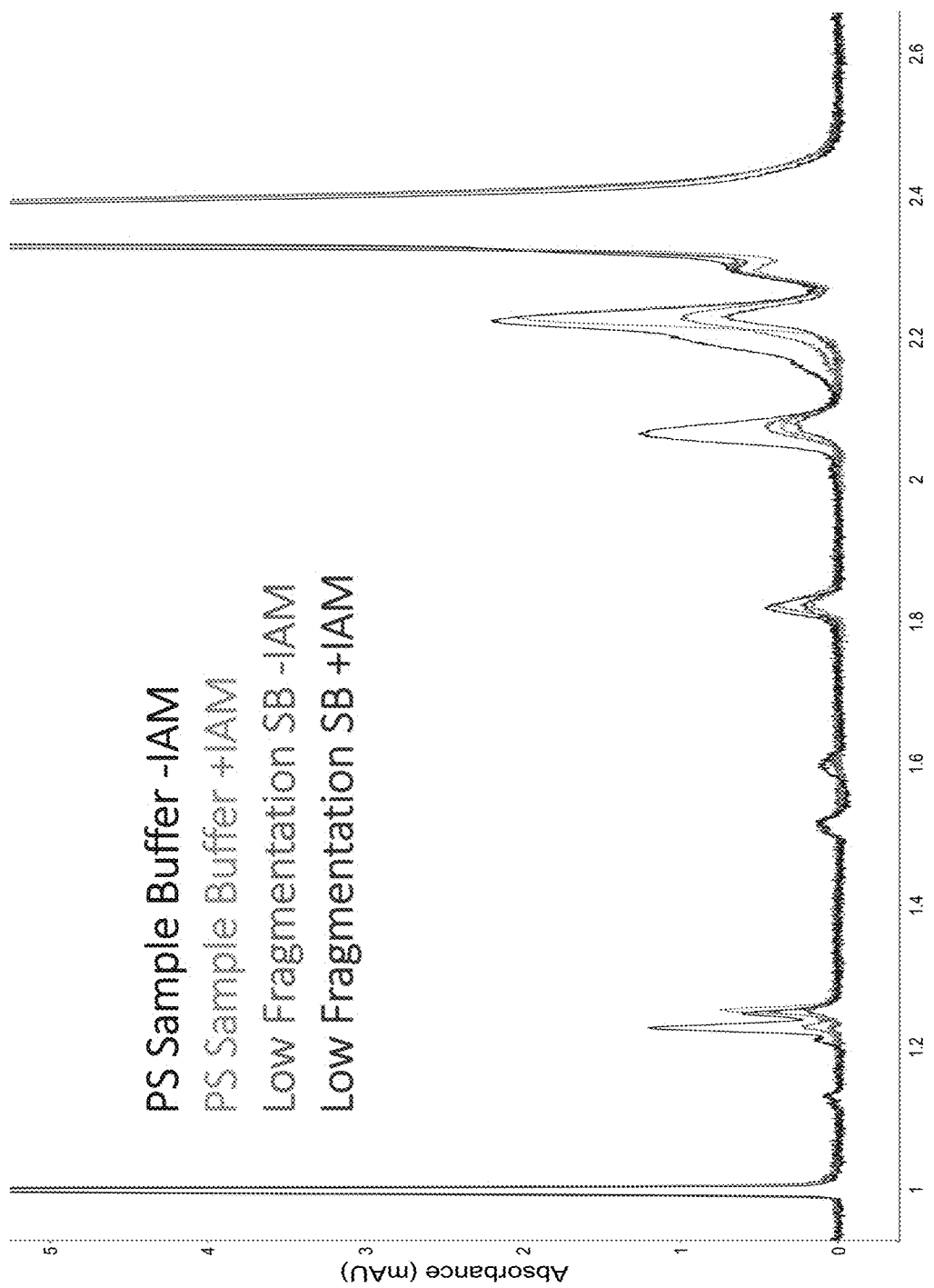
FIG. 6 shows testing of CE-SDS resolution of trastuzumab in final sample buffer candidate ("Low Fragmentation SB") under non-reducing treatment, where sample is final sample buffer candidate is treated with iodoacetamide (IAM) and heated. Final sample buffer candidate decreases incubation-induced fragmentation.

The final sample buffer candidate showed comparable performance to ProteinSimple® sample buffer (Maurice CE-SDS 1X Sample Buffer) in terms of peak shape (FIGS. 5A-5B). But the final sample buffer candidate exhibited improved (decreased) fragmentation of exemplary protein, biosimilar trastuzumab biosimilar when tested with and without alkylation was tested. Specifically, use of final sample buffer candidate without IAM resulted in fewer size variants than sample prepared in standard sample buffer; and use of final sample buffer candidate with IAM resulted in yet fewer size variants than sample prepared in standard sample buffer, or than sample prepared in final sample buffer candidate without IAM.

Figure 7:
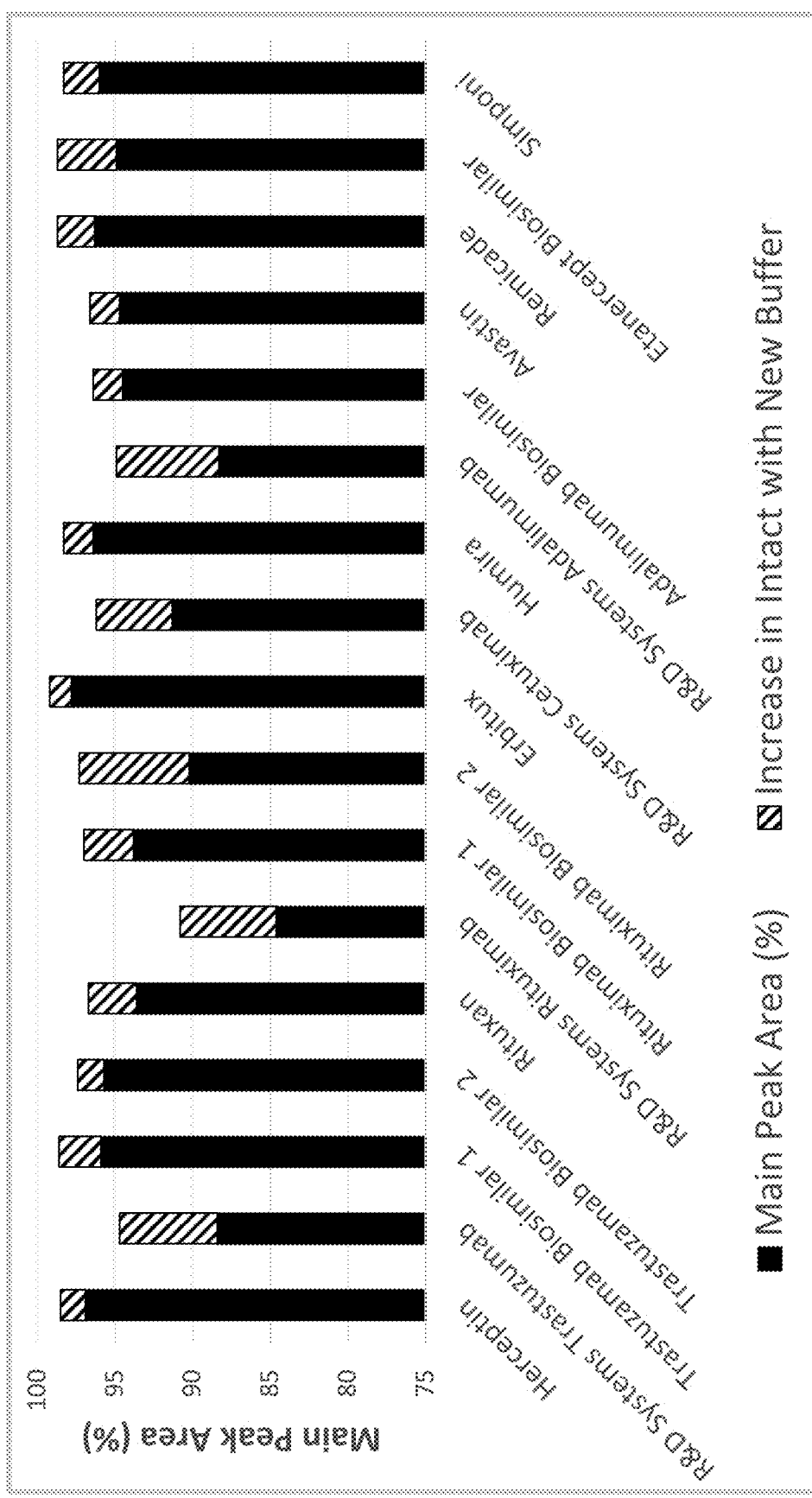
FIG. 7 summarizes testing of other monoclonal antibodies (mAbs) in the final sample buffer candidate.
Figure 8A:
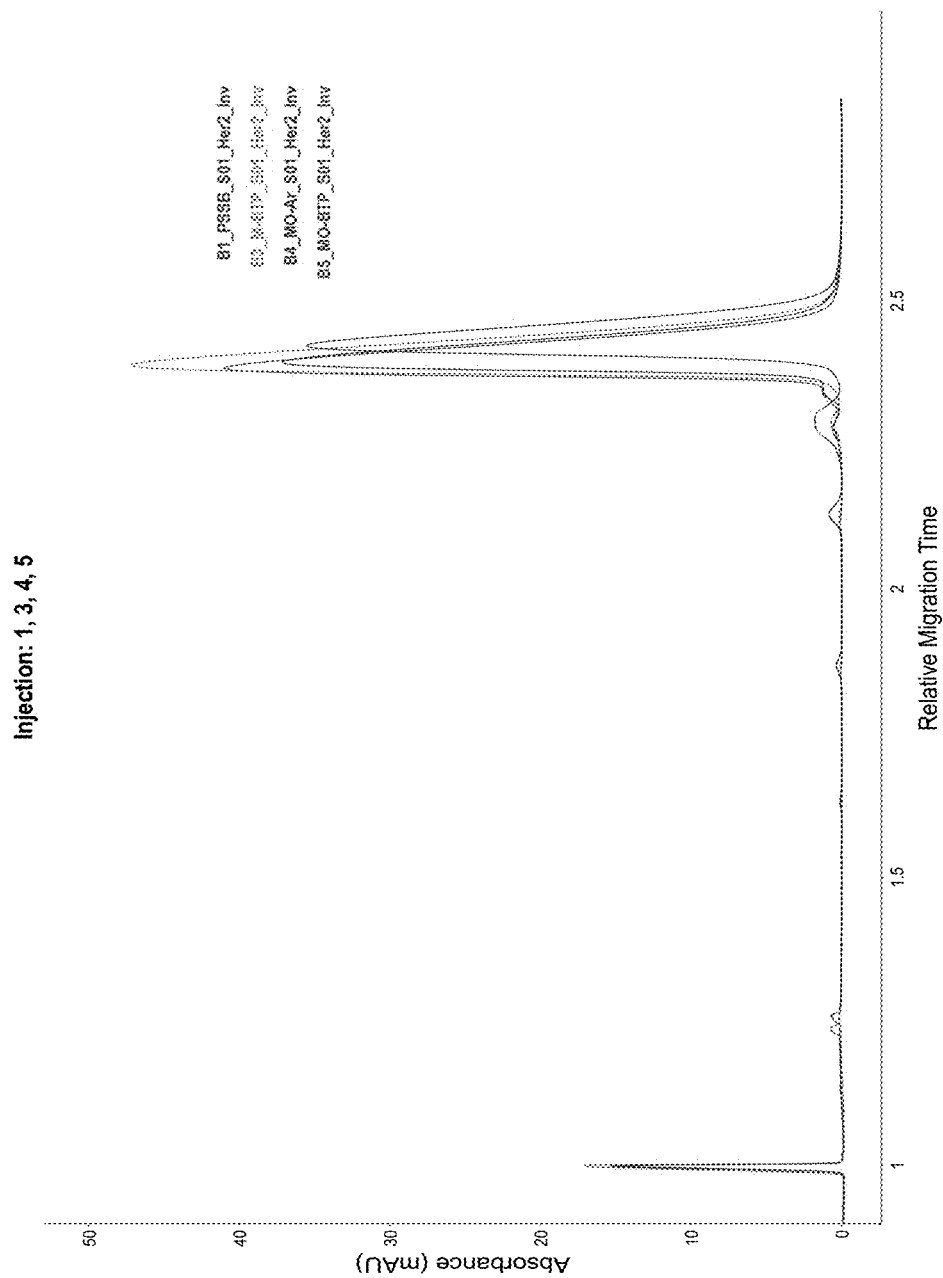
FIGS. 8A-8B, 9A-9B, 10A-10B, and 11A-11B show results in various buffer candidates for biologic drugs.
Figure 8B:
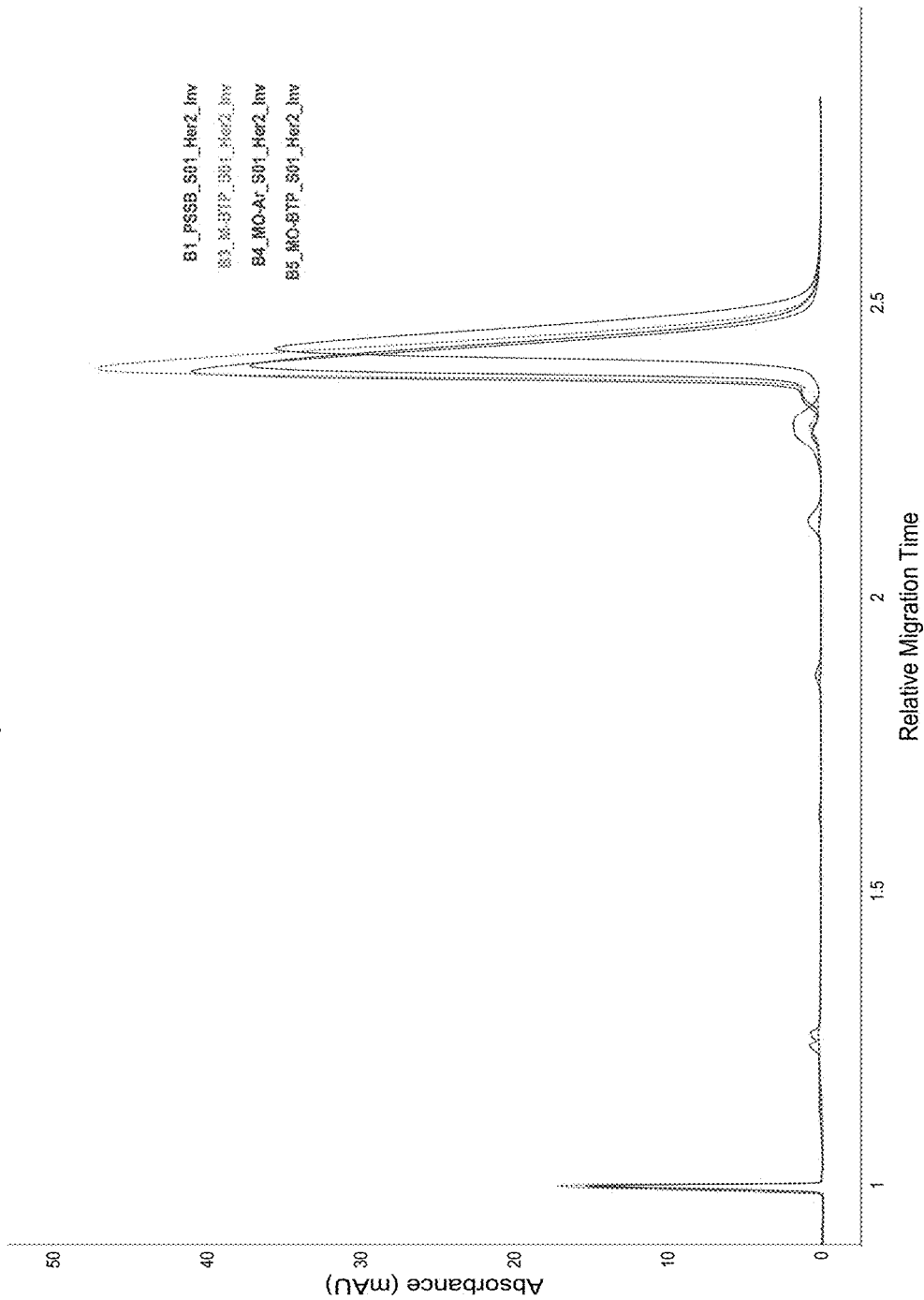
Figure 8C:
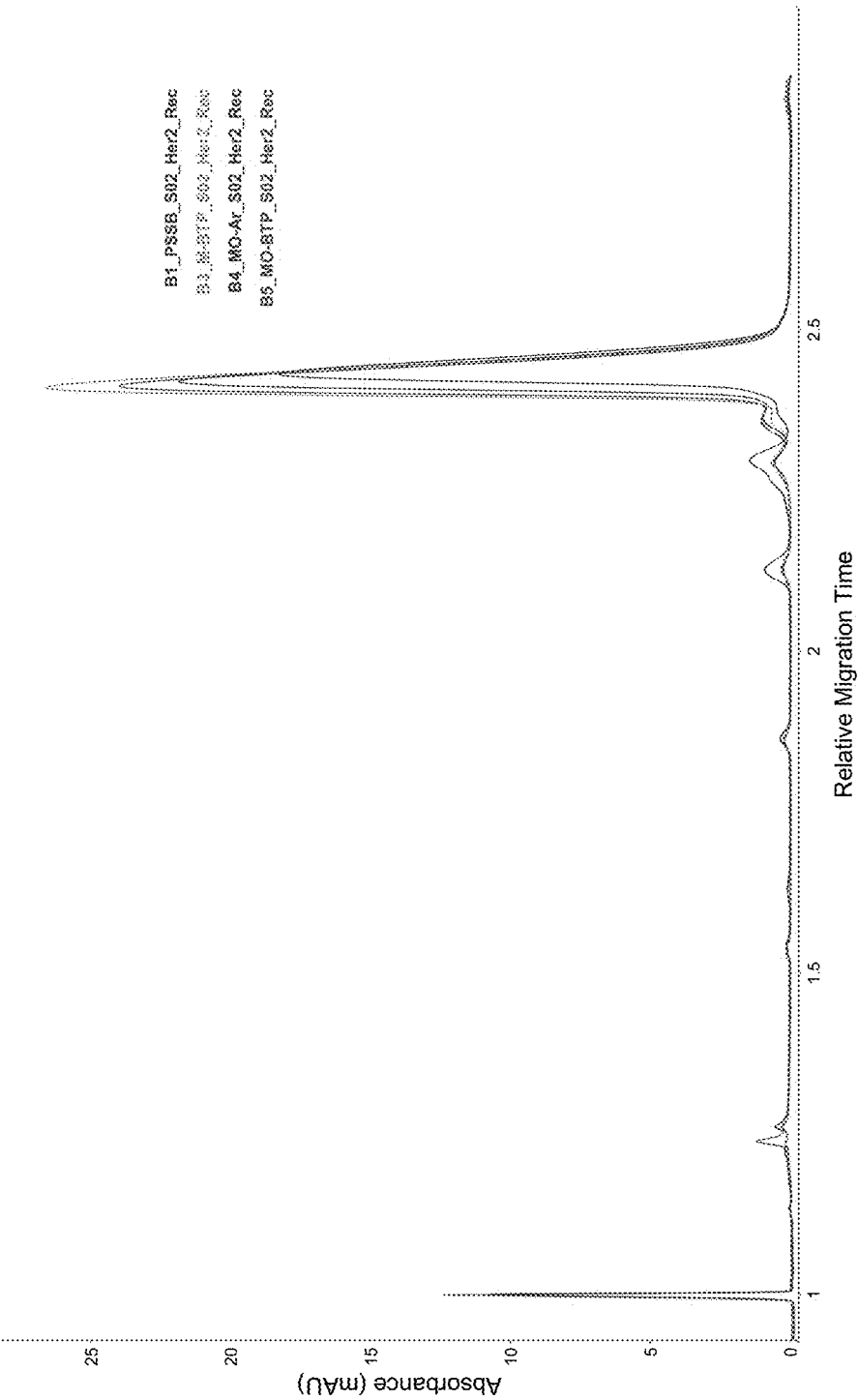
FIG. 8C shows trastuzumab innovator; zoomed in FIG. 8D.
Figure 8D:
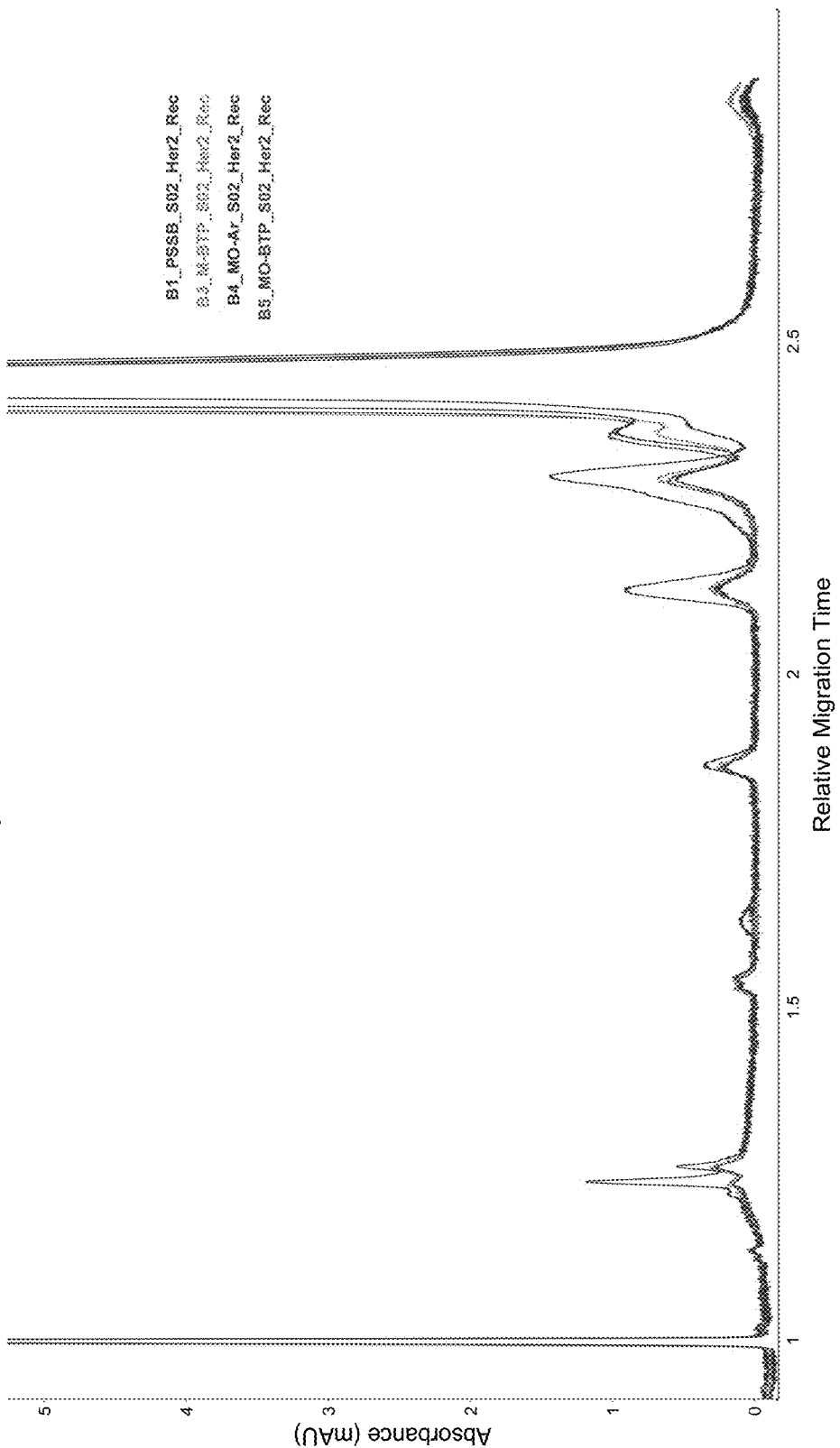
Figure 9A:
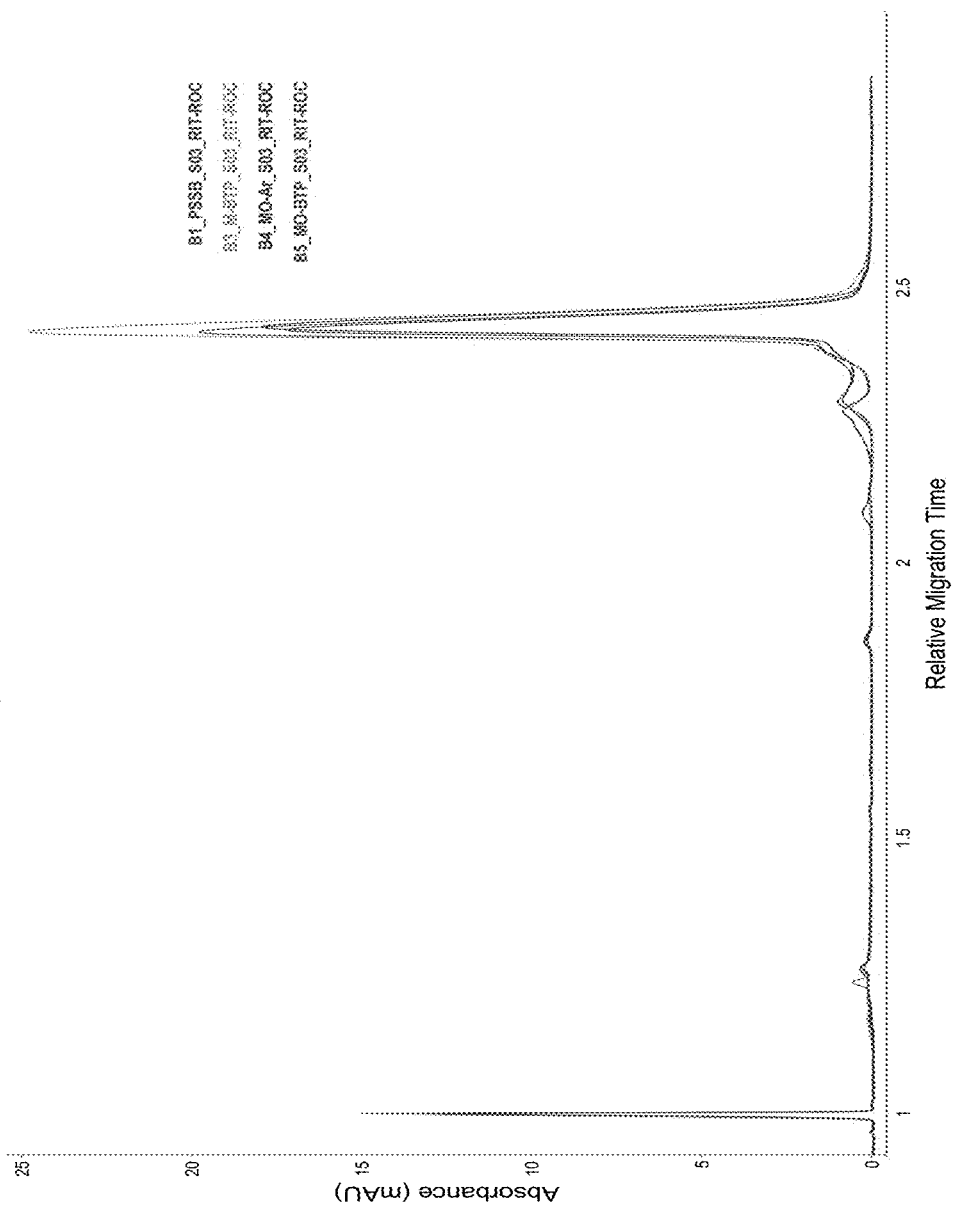
Figure 9B:
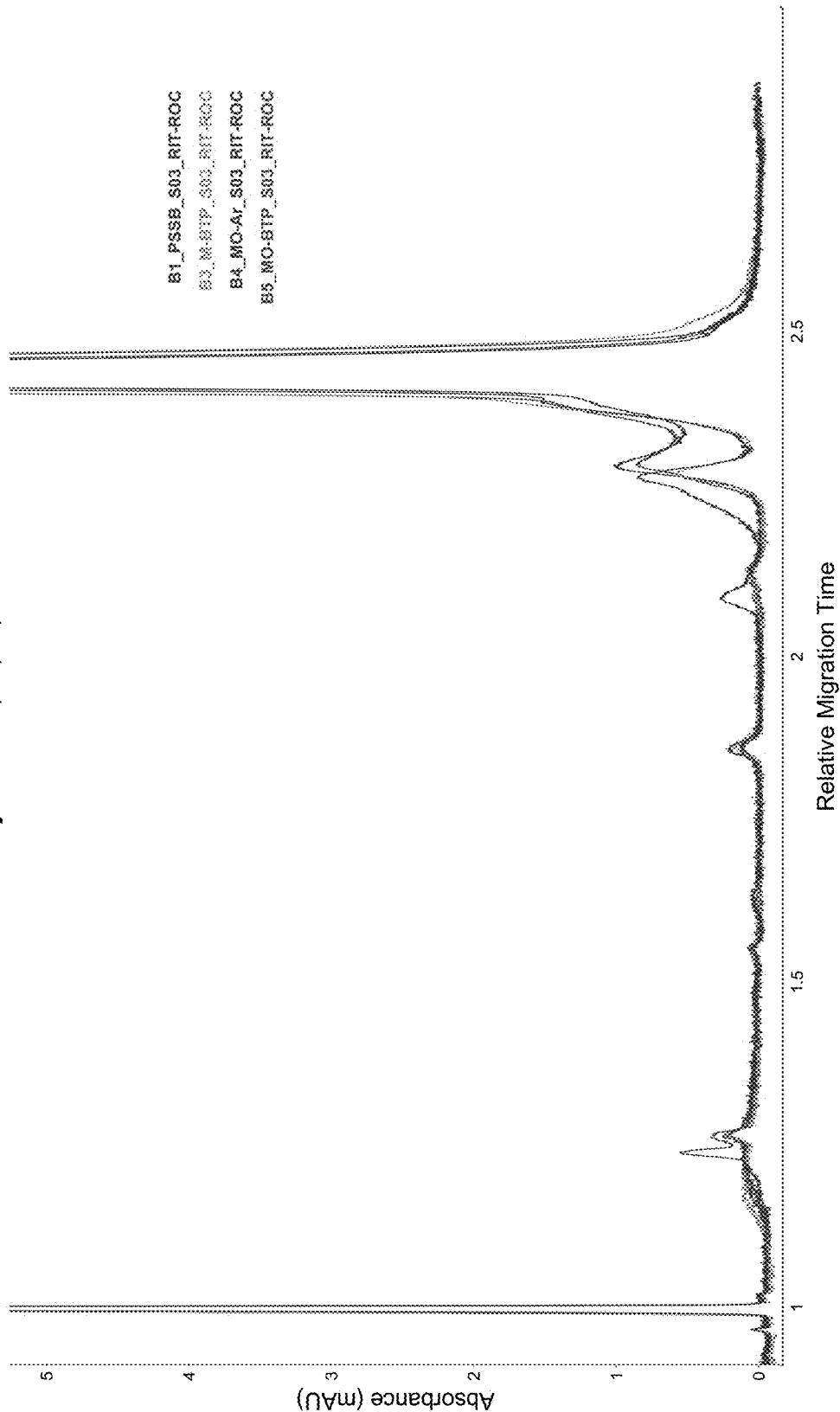
Figure 10A:
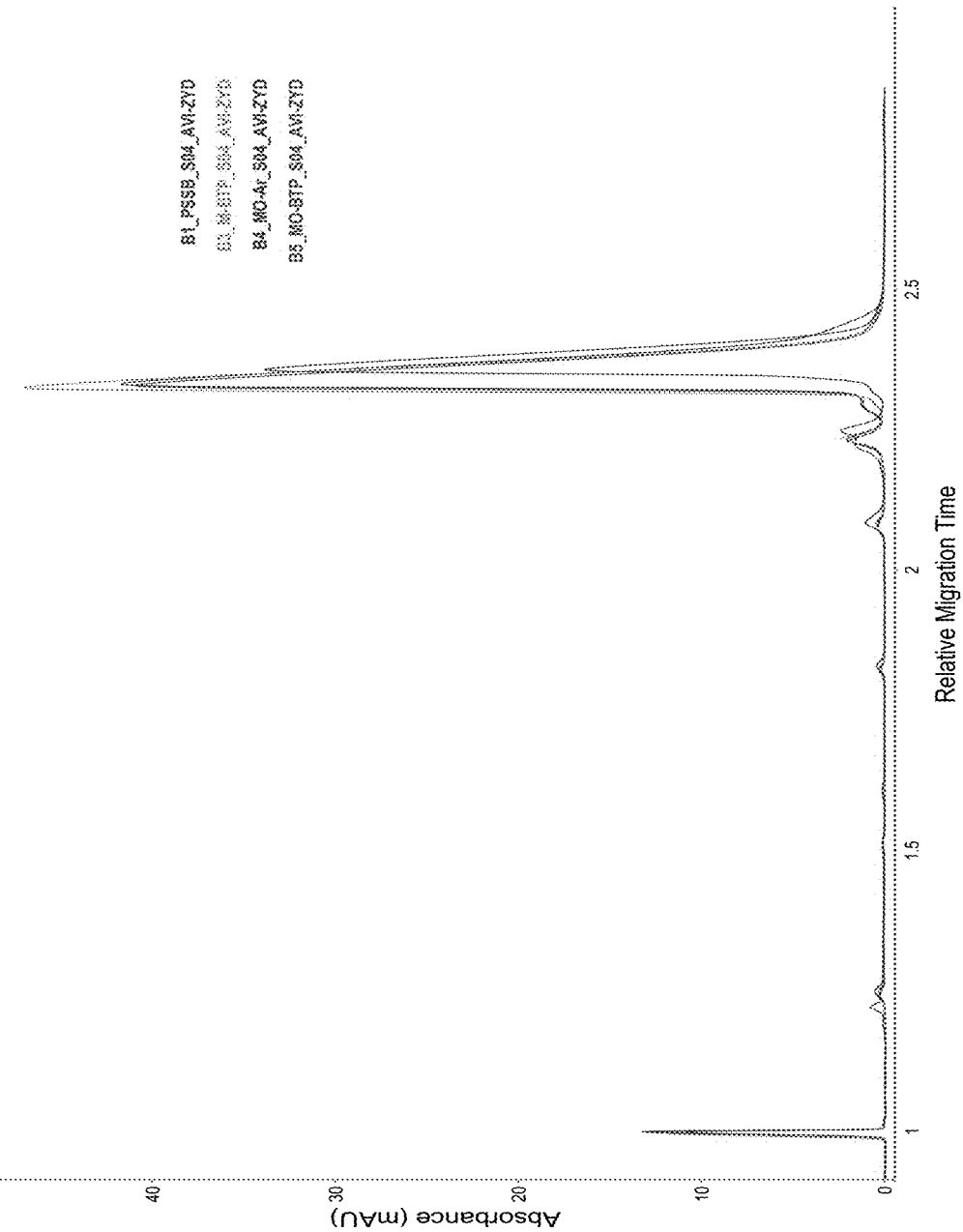
Figure 10B:
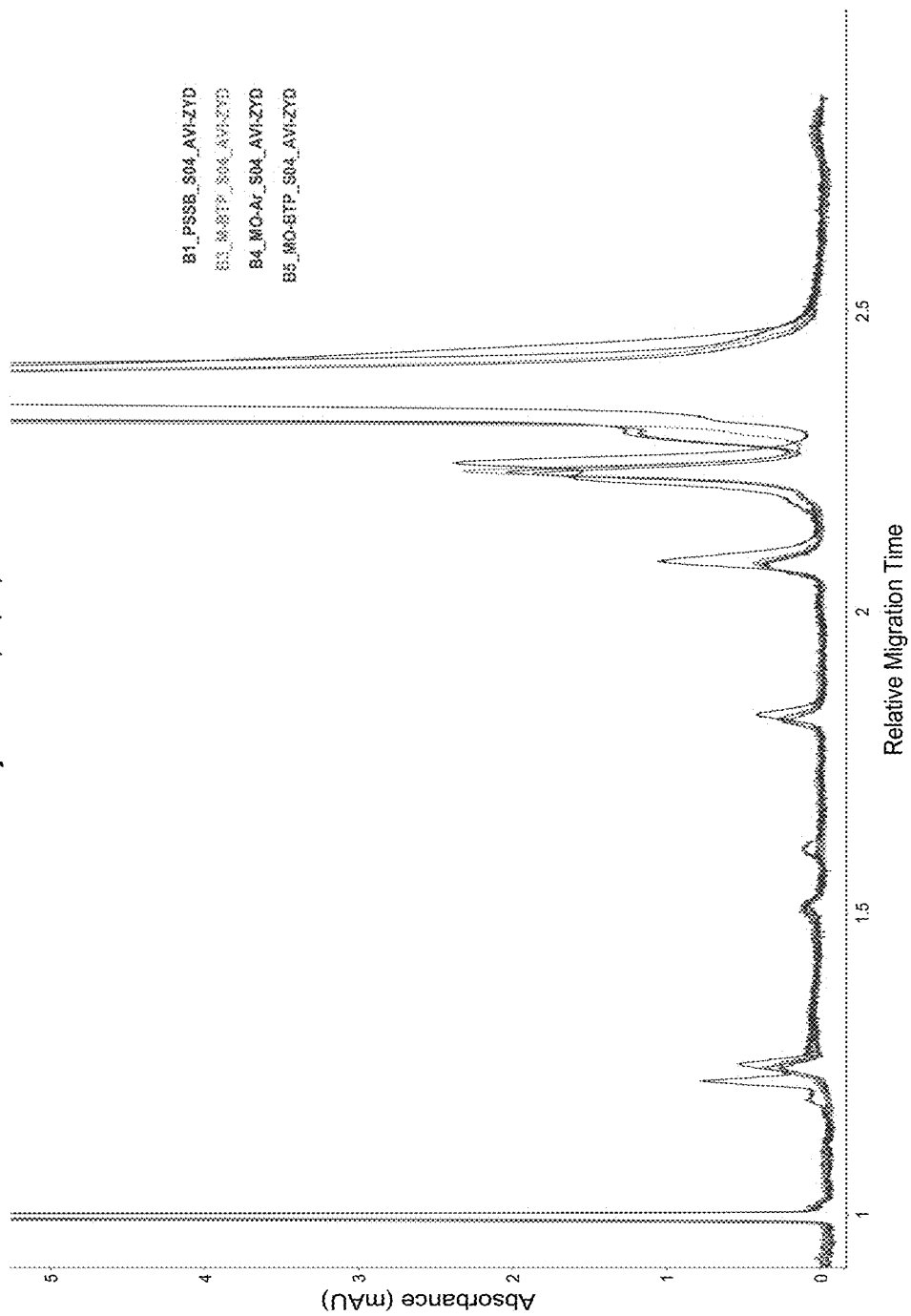
Figure 11A:
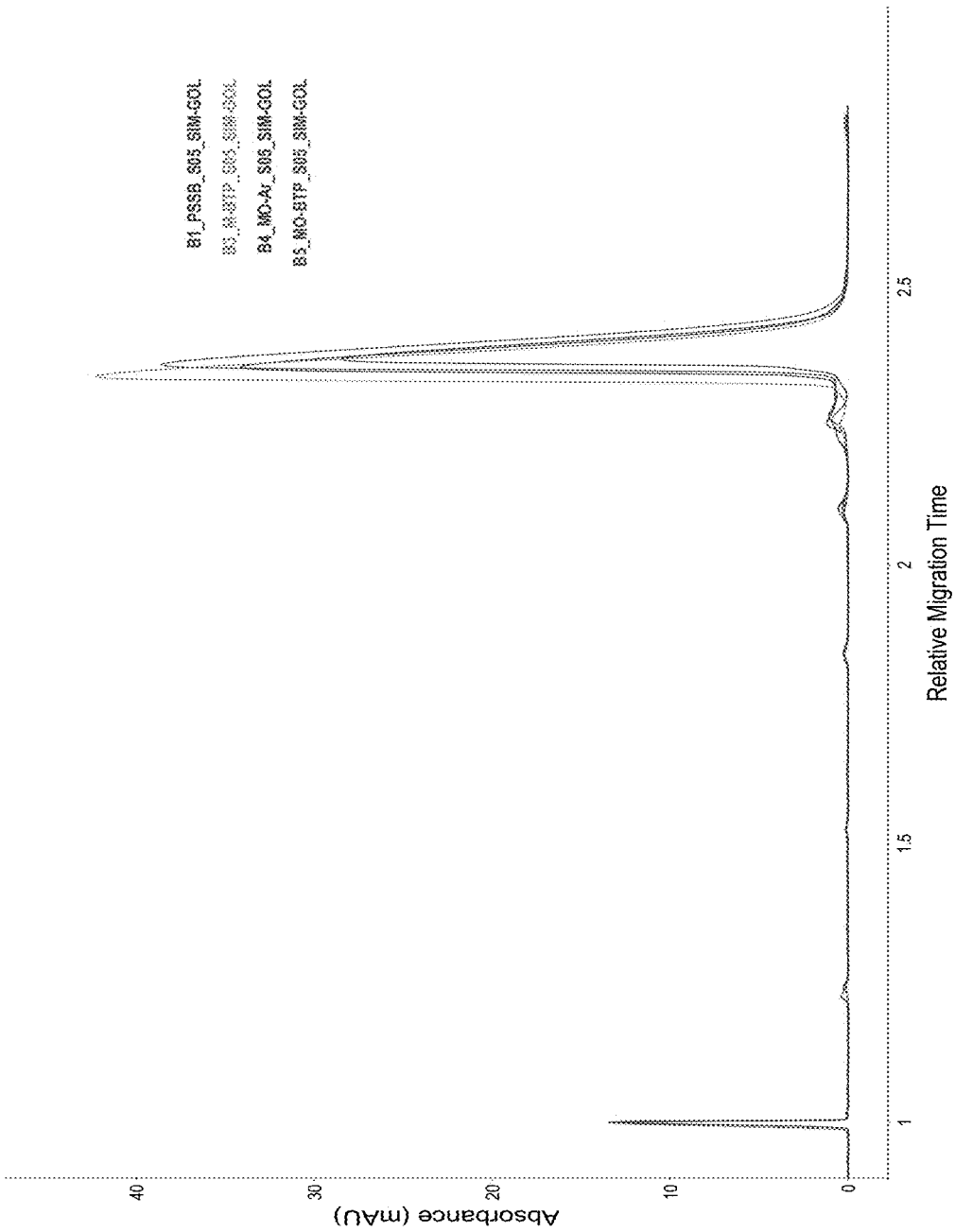
Figure 11B:
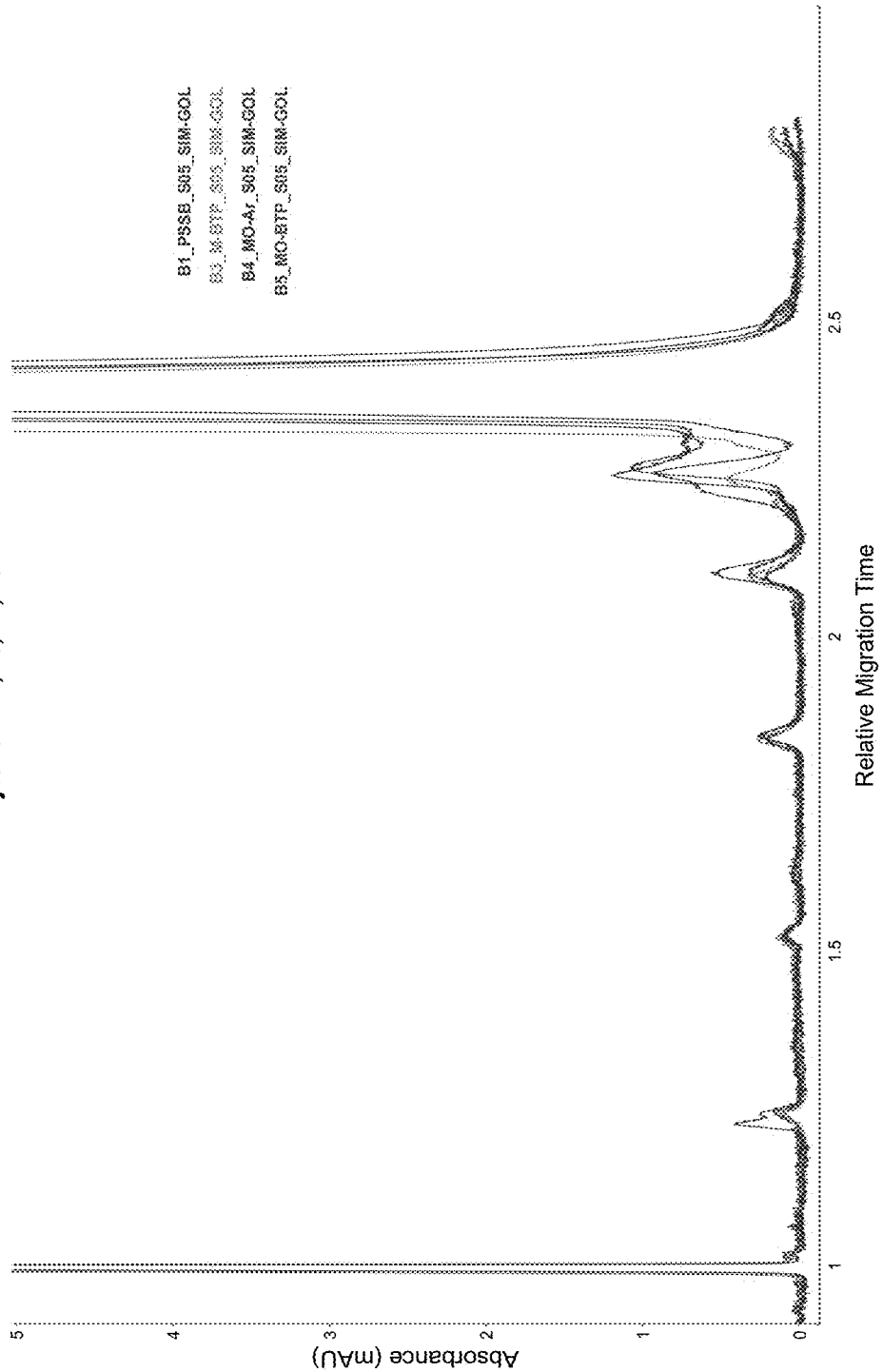

This final candidate was tested with a number of biosimilars or innovator biologics and found to be beneficial to all of them that were tested. FIG. 7 summarizes results for tested analytes, with underlying data shown in FIGS. 8A-8B, 9A-9B, 10A-10B, and 11A-11B. The final sample buffer candidate minimizes fragmentation for all therapeutic molecules tested. Each sample was run with the PS SB and the final sample buffer candidate in sequential injections. The difference in intact peak area for each molecule was determined and represented as the increase in % Main Peak Area (striped pattern in bar graph).

Figure 12A:
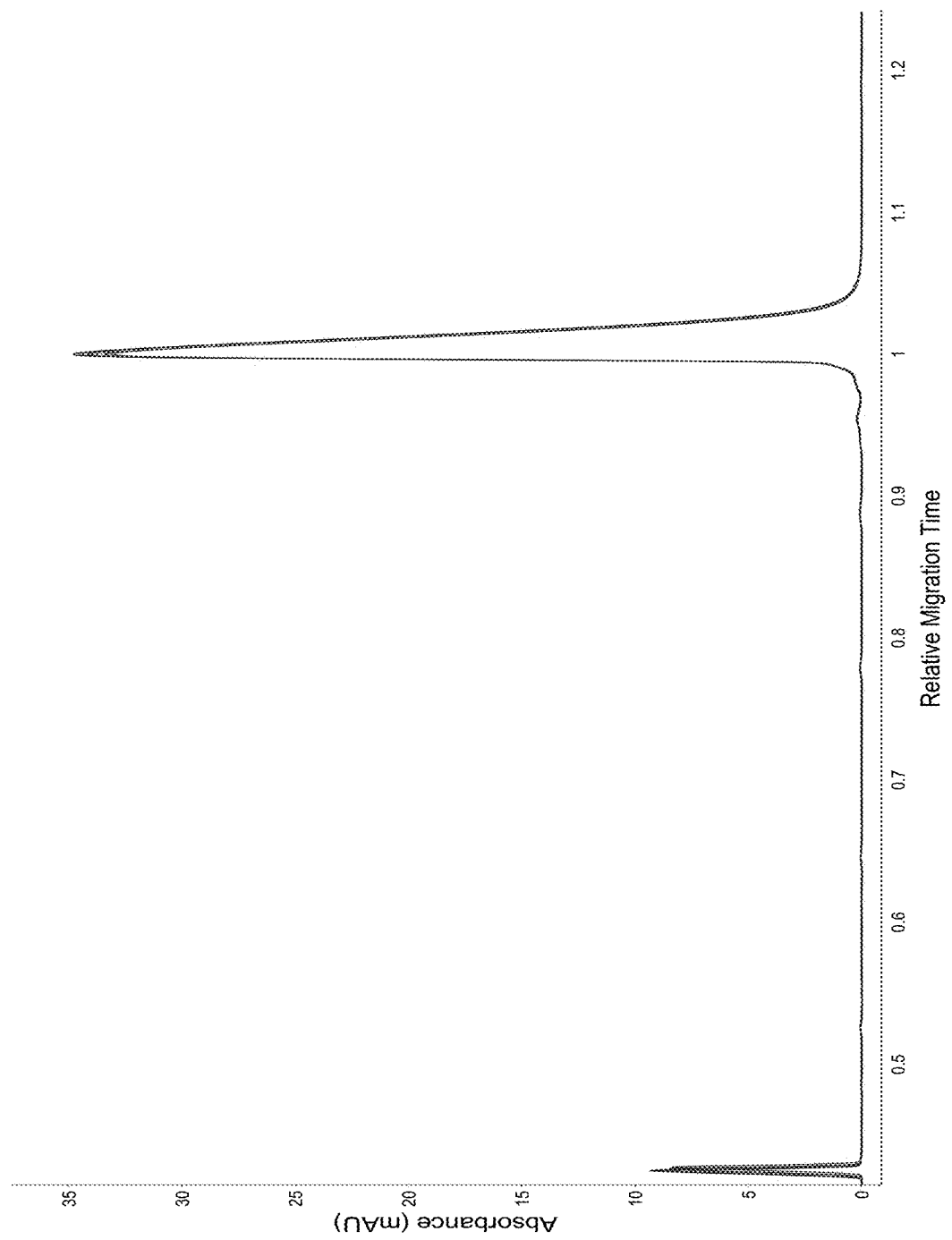
FIGS. 12A-12B show validation of final sample buffer candidate using the Monoclonal Antibody Reference Material 8671 (NISTmAb).
Figure 12B:
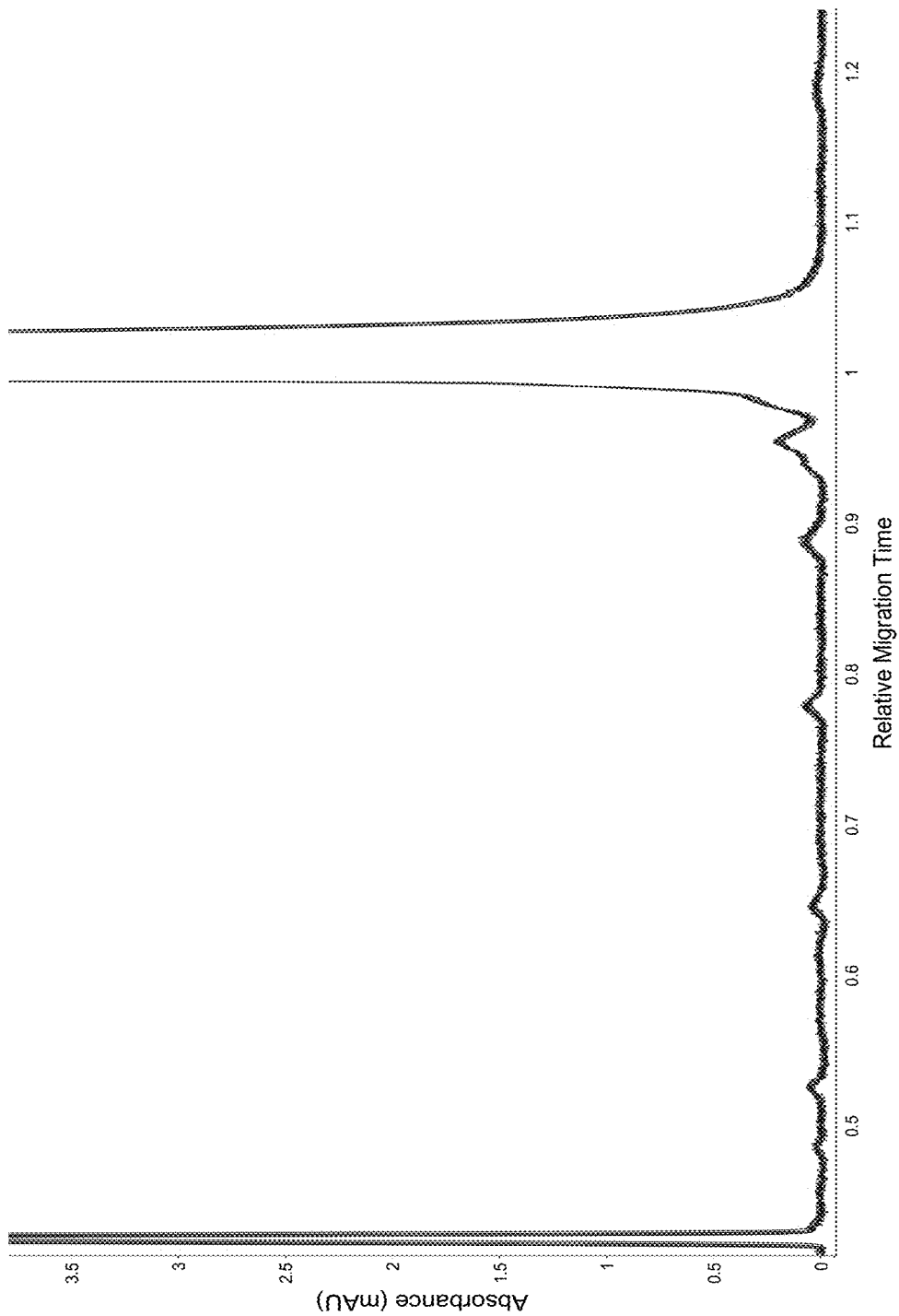

Lastly, the final candidate was validation using the Monoclonal Antibody Reference Material 8671 (NISTmAb). The final candidate demonstrated high repeatability and low fragmentation of NISTmAb over at least nine injections (Table 9 and FIGS. 12A-12B).

TABLE 9

| Validation with NISTmAB | | |
|---|---|---|
| | % CPA | |
| NISTmAb NR (N = 9) | LMWS | Intact |
| Average | 1.08 | 98.92 |
| Std. Dev. | 0.06 | 0.06 |
| % CV | 5.47 | 0.06 |

While various embodiments have been described above, it should be understood that they have been presented by way of example only, and not limitation. It should be understood that run buffer can be fluidically coupled to the capillary by any suitable means. While the embodiments have been particularly shown and described, it will be understood that various changes in form and details may be made. Although various embodiments have been described as having particular features and/or combinations of components, other embodiments are possible having a combination of any features and/or components from any of embodiments as discussed above.

All documents, patents, patent applications, publications, product descriptions, and protocols which are cited throughout this application are incorporated herein by reference in their entireties for all purpose.

The invention claimed is:

1. A kit comprising:
   (i) a capillary electrophoresis sodium dodecyl sulfate (CE-SDS) sample loading buffer, comprising:
      a buffered aqueous solution having a pH between 6.0 and 7.7 and configured to load a sample into a capillary for capillary electrophoresis, the buffered aqueous solution including:
      (i-a) an acidic buffer selected from the group consisting of: 2-(N-morpholino)ethanesulfonic acid (MES), 3-(N-morpholino)propanesulfonic acid (MOPS), 2-Hydroxy-3-morpholinopropanesulfonic acid (MOPSO), and N-(2-Acetamido)-2-aminoethanesulfonic acid (ACES); and
      (ii-a) Bis-Tris Propane (BTP); and
   (ii) instructions for use in CE-SDS electrophoresis.

2. The kit of claim 1, wherein the sample is a polypeptide sample.

3. The kit of claim 1, wherein the acidic buffer is selected from the group consisting of MOPS and MOPSO.

4. The kit of claim 1, wherein the CE-SDS sample loading buffer has a pH of about 7.0 to about 7.4.

5. The kit of claim 1, wherein the CE-SDS sample loading buffer has a conductivity of 2.0 mS/cm or less.

6. The kit of claim 1, wherein the concentration of the at least one of 2-(N-morpholino)ethanesulfonic acid (MES), 3-(N-morpholino)propanesulfonic acid (MOPS), 2-Hydroxy-3-morpholinopropanesulfonic acid (MOPSO), and N-(2-Acetamido)-2-aminoethanesulfonic acid (ACES) is about 50 mM.

7. The kit of claim 1, wherein the CE-SDS sample loading buffer further comprises one or more of ethylenediaminetetraacetic acid (EDTA), sodium dodecylsulfate (SDS), and glycerol.

8. The kit of claim 1, wherein the CE-SDS sample loading buffer is compatible with a capillary electrophoresis assay with sodium dodecylsulfate (CE-SDS).

9. The kit of claim 1, wherein the CE-SDS sample loading buffer is configured such that capillary electrophoresis with sodium dodecylsulfate (CE-SDS) performed using the sample loading buffer has sensitivity at least 90% as great as the sensitivity of CE-SDS using 100 mM Tris-HCl, 1.0% SDS, pH 9.0 as the sample loading buffer.

10. The kit of claim 1, wherein the CE-SDS sample loading buffer is configured such that capillary electrophoresis with sodium dodecylsulfate (CE-SDS) performed using the sample loading buffer has sensitivity at least 90% as great as the sensitivity of CE-SDS using 100 mM Tris-HCl, 1.0% SDS, pH 9.0 as the sample loading buffer.

11. The kit of claim 2, wherein the polypeptide analyte comprises rituximab or golimumab.

12. A kit comprising:
   (i) a capillary electrophoresis sodium dodecyl sulfate (CE-SDS) sample loading buffer, comprising:
      a buffered aqueous solution having a pH between 6.0 and 7.7 and configured to load a sample into a capillary for capillary electrophoresis, the buffered aqueous solution including:
      (i-a) an acidic buffer selected from the group consisting of: 2-(N-morpholino)ethanesulfonic acid (MES), 3-(N-morpholino)propanesulfonic acid (MOPS), 2-Hydroxy-3-morpholinopropanesulfonic acid (MOPSO), and N-(2-Acetamido)-2-aminoethanesulfonic acid (ACES); and
      (ii-a) Bis-Tris Propane (BTP); and
   (ii) a capillary suitable for CE-SDS.

13. The kit of claim 12, wherein the sample is a polypeptide sample.

14. The kit of claim 12, wherein the acidic buffer is selected from the group consisting of MOPS and MOPSO.

15. The kit of claim 12, wherein the CE-SDS sample loading buffer has a pH of about 7.0 to about 7.4.

16. The kit of claim 12, wherein the CE-SDS sample loading buffer has a conductivity of 2.0 mS/cm or less.

17. The kit of claim 12, wherein the concentration of the at least one of 2-(N-morpholino)ethanesulfonic acid (MES), 3-(N-morpholino)propanesulfonic acid (MOPS), 2-Hydroxy-3-morpholinopropanesulfonic acid (MOPSO), and N-(2-Acetamido)-2-aminoethanesulfonic acid (ACES) is about 50 mM.

18. The kit of claim 12, wherein the CE-SDS sample loading buffer further comprises one or more of ethylenediaminetetraacetic acid (EDTA), sodium dodecylsulfate (SDS), and glycerol.

19. The kit of claim 12, wherein the CE-SDS sample loading buffer is compatible with a capillary electrophoresis assay with sodium dodecylsulfate (CE-SDS).

20. The kit of claim 12, wherein the CE-SDS sample loading buffer is configured such that capillary electrophoresis with sodium dodecylsulfate (CE-SDS) performed using the sample loading buffer has sensitivity at least 90% as great as the sensitivity of CE-SDS using 100 mM Tris-HCl, 1.0% SDS, pH 9.0 as the sample loading buffer.

21. The kit of claim 12, wherein the CE-SDS sample loading buffer is configured such that capillary electrophoresis with sodium dodecylsulfate (CE-SDS) performed using the sample loading buffer has sensitivity at least 90% as great as the sensitivity of CE-SDS using 100 mM Tris-HCl, 1.0% SDS, pH 9.0 as the sample loading buffer.

22. The kit of claim 13, wherein the polypeptide analyte comprises rituximab or golimumab.

* * * * *